(12) United States Patent
Alba

(10) Patent No.: US 7,257,518 B2
(45) Date of Patent: Aug. 14, 2007

(54) FUNDAMENTAL METHOD AND ITS HARDWARE IMPLEMENTATION FOR THE GENERIC PREDICTION AND ANALYSIS OF MULTIPLE SCATTERING OF WAVES IN PARTICULATE COMPOSITES

(75) Inventor: Felix Alba, Murray, UT (US)

(73) Assignee: Felix Alba Consultants, Inc., Murray, UT (US)

( * ) Notice: Subject to any disclaimer, the term of this patent is extended or adjusted under 35 U.S.C. 154(b) by 768 days.

(21) Appl. No.: 09/796,004

(22) Filed: Feb. 28, 2001

(65) Prior Publication Data

US 2003/0167156 A1 Sep. 4, 2003

(51) Int. Cl.
- *G06F 7/48* (2006.01)
- *G06G 9/45* (2006.01)
- *G06G 7/60* (2006.01)
- *G06F 17/50* (2006.01)

(52) U.S. Cl. .......... 703/2; 703/1; 703/5; 703/6; 703/22

(58) Field of Classification Search .......... 703/2, 703/5, 6, 22; 73/61.75
See application file for complete search history.

(56) References Cited

U.S. PATENT DOCUMENTS

| | | | | |
|---|---|---|---|---|
| 5,121,629 A | * | 6/1992 | Alba | .......... 73/61.41 |
| 5,619,324 A | * | 4/1997 | Harvill et al. | .......... 356/336 |
| 5,818,583 A | * | 10/1998 | Sevick-Muraca et al. | ... 356/336 |
| 6,109,098 A | * | 8/2000 | Dukhin et al. | .......... 73/64.42 |
| 6,119,510 A | * | 9/2000 | Carasso et al. | .......... 73/61.75 |

OTHER PUBLICATIONS

"Scatter.com" www.scatter.com 1999-2004. p. 1-7.*
Kew-M., "Piercing Sounds" IEEE 1996, p. 74.*
Real Time, A Two-Dimensional Electromagnetic Field Simulator, CRC Press, (800) 272-7737.
P.C. Waterman & R. Truell, "Multiple Scattering of Waves", J. Math. Physics, vol. 2, No. 4, Jul.-Aug. 1961.
P.C. Waterman & R. Truell, "Multiple Scattering of Waves", J. Math. Physics, vol. 2, No. 4, Jul.-Aug. 1961, p. 524.

(Continued)

*Primary Examiner*—Anthony Knight
*Assistant Examiner*—Thomas H. Stevens

(57) ABSTRACT

This invention relates to a method and apparatus for the fundamental prediction, analysis, and parametric studies of the interaction of multiply scattered waves of any nature (acoustic, electromagnetic, elastic) with particulate composites (solid or fluid particulate phases included in a solid or fluid phase). It comprises of: a) a Prediction Engine 21 to predict the composite physical attributes from those of the constituent phases, b) an Inversion Engine 22 to estimate a subset of the attributes of the constituent phases and composite from the rest of those attributes, and c) an ergonomic Graphical Interface 23 to enable the user to easily set up complex simulation experiments for the analysis, and synthesis of real systems in which generic waves interact with composites. The Prediction Engine 22 is suitable for integration into existing acoustic or optical particle size analyzers to thereby extending their concentration ranges by at least two orders of magnitude.

20 Claims, 6 Drawing Sheets

OTHER PUBLICATIONS

P. Lloyd & M.V. Berry, "Wave Propagation through and Assembly of Spheres IV. Relations between Different Multiple Scattering Theories", Proc. Phys. Soc., vol. 91, 1967, pp. 679 & 683.

A. Ishimaru, "Wave Propagation and Scattering in Ramdom Media", Academic Press, 1978, pp. 148-149 & 175-181.

L. Tsang et al, "Multiple Scattering of Acoustic Waves by Random Distribution of Discrete Scatterers with the Quasicrystalline . . . ", J.A.S.A., 71(3), Mar. 1982, pp. 552-558.

V.K. Varadan et al, "A Multiple Scattering Theory for Elastic Wave Propagation in Discrete Random Media", J.A.S.A. 77(2), Feb. 1985, pp. 375-385.

V.V. Varadan et al, "Multiple Scattering Theory for . . . ", Multiple Scattering of Waves in Random Media and Random Rough Surfaces, The Pennsylvania State University, 1985, pp. 941-951.

E. Sevick-Muraca et al, "Photon-Migration Measurement of Latex Size Distribution in Concentrated Suspensions", AlChe Journal, vol. 43, No. 3, Mar. 1997, pp. 655-664.

F. Alba et al, "Ultrasound Spectroscopy: A . . . ", Handbook on Ultrasonic and Dieelectric Characterization Techniques for Suspended Particulates, The American Ceramic Soc., 1998, pp. 111-127.

V.K. Varadan et al., "A Multiple Scattering Theory for Elastic Wave Propagation in Discrete Random Media", J.A.S.A. 77 (2), Feb. 1985, pp. 375-385.

E.D. Hirleman, Arizona State University, "A General Solution to the Inverse Near-Forward Scattering Particle Sizing Problem in Multiple Scattering Environments: Theory Abstract", pp. 159-168.

* cited by examiner

FUNDAMENTAL METHOD AND ITS HARDWARE IMPLEMENTATION FOR THE GENERIC PREDICTION AND ANALYSIS OF MULTIPLE SCATTERING OF WAVES IN PARTICULATE COMPOSITES

Attached hereto there are two identical CD-R disks (labeled Copy 1 and Copy 2), hereby incorporated by reference as a computer program listing appendix, and containing the following files: a) Scatterer.exe (Oct. 22, 2001, 2.89 MB) b) PredictionEngine.exe (Oct. 15, 2001, 36.0 KB), c) ScattererDLL.dll (Oct. 22, 2001, 656 KB), d) Setup.1st (Oct. 22, 2001, 20.0 KB), e) Scatterer.cab (Oct. 22, 2001, 14.7 MB), f) Setup.exe (Mar. 14, 2000, 138 KB), and g) DataAuto.exe (Aug. 28, 2001, 218 KB). By following industry-standard installation procedures in a computer operating under a member of the MS-Windows® family of operating systems and a Pentium® III or higher equivalent processor, full disclosure for the current invention is enhanced, and its operability can be confirmed with actual experimental data provided in the disk. A commercial product based on this invention, to be called SCATTERER™, will be marketed in the near future. The copyright owner has no objection to legal use and reproduction of this patent document and attached CD-R disks, as they appear in the Patent and Trademark Office records, reserving otherwise all rights.

BACKGROUND

1. Field of Invention

This invention relates to a method and its hardware implementation for the fundamental prediction, analysis, and parametric studies of the interaction of multiply scattered waves of any nature (acoustic, electromagnetic, elastic) with particulate composites (solid or fluid particulate phases included in a solid or fluid continuous phase). Any embodiment for the present invention constitutes a powerful research and development tool in a vast variety of engineering and scientific fields dealing with wave propagation in composites (e.g. foods, paints, cosmetics, mineral slurries, pharmaceuticals, etc). The METAMODEL™ Prediction Engine 21, a crucial component of this invention (FIG. 1), is suitable for integration into existing acoustic or optical particle size analyzers to thereby extending their particle concentration ranges by at least two orders of magnitude.

2. Discussion of Prior Art

Prior art for the present invention pertains to three fields: a) Tools to assist in scientific and engineering work; b) Theoretical physics; and c) Instrumentation for particle size measurement. Several tools to assist in the modeling, analysis, and parametric studies of physical systems are known in the prior art and available in the market. Some of them are general mathematical tools with thousands of functions in calculus, linear algebra, ordinary differential equations, partial differential equations, Fourier analysis, dynamic systems, etc. An incomplete list includes MATLAB™ ([C1], The MathWorks, Inc), Maple V® ([C2], Waterloo Maple Software), SCIENTIFIC WORKPLACE™ ([C3], TCI Software Research), MathCad™ ([C4], MathSoft, Inc.), and Mathematica® ([C5], Wolfram Research, Inc.). These systems constitute, in a hierarchy of research and development tools, a next level up from e.g. the well-known IMSL FORTRAN/C library of scientific routines ([C6], Visual Numerics, Inc.). By becoming a little more specific in scope, they offer a higher-level language to the user, reducing the need for proficiency in computer programming and increasing the efficiency with which the scientist/engineer solves his/her problems. Some other systems are even more specific like FEMLAB® ([C7], COMSOL, Inc.) or MaX-1 ([C8], A visual Electromagnetics Platform, J. Wiley) or Real Time ([C9], A Two-Dimensional Electromagnetic Field Simulator, CRC Press). The last two systems are overly specific simulators, as they cover only certain aspects of electromagnetic waves with no flexibility offered to modeling their multiple scattering in particulates. The first one, FEMLAB®, using MATLAB™ as a software platform, offers to the user a less specific high-level language oriented towards the solution of partial differential equations using the finite element technique for problems in physics and engineering. It allows the user to create a suitable mathematical model for the physical problem at hand from available building blocks (partial differential equations, functional relationships, etc.) in an ample variety of disciplines including acoustics, fluid dynamics, structural mechanics, heat transfer, chemical processing, and electromagnetics. After a short training, the user only needs to be concerned with physics and engineering, and is required no major proficiency in computer programming and numerical intricacies. However, no pre-built modeling blocks for multiple scattering of waves in particulate composites are available either.

All these systems in the prior-art are either exceedingly general or overly specific to efficiently solve the multiply interleaved wave equations required to accurately predict the multiple scattering of waves in particulates. In order to take advantage of those existing tools, it would inevitably require an expert on both the physics and the mathematics of the problem who—in addition—would have to command the novel know-how to be disclosed in this specification, plus unacceptable computer time and human effort. A system tackling all those intricate physico-mathematical aspects of the problem, and making them transparent to the regular physicist/engineer has been clearly in need for many years. The current invention provides such a tool.

An essential part of the present invention is the ability to accurately predict the composite physical attributes (e.g. wave attenuation, wave velocity, scattered intensity, etc) when the physical attributes of the constituent phases (i.e. the particles and the host medium) are known. Two distinct approaches have historically developed in trying to mathematically model scattering of waves with particulates. One is microscopic (fundamental) and called the analytical wave-scattering theory; the other is macroscopic (phenomenological) and called the transport theory or radiative transfer theory ([22] A. Ishimaru, "Wave Propagation and Scattering in Random Media", Academic Press, 1978; [48] F. Alba et al, "Ultrasound Spectroscopy: A Sound Approach to Sizing of Concentrated Particulates", Handbook on Ultrasonic and Dielectric Characterization Techniques for Suspended Particulates, The American Ceramic Society, 1998). The former starts with the wave equation, rigorously predicts the scattering of a wave with a single particle in the medium, and statistically describes the interaction between all the scattered fields around all the particles, to arrive to expected values for the attributes of the composite in terms of the attributes of its constituents. It is a mathematically rigorous fundamental approach and, as a consequence, all the multiple scattering, diffraction, and interference effects are contemplated with the broad validity and accuracy range inherent to a first-principle technique. This is the physico-mathematical background of the current invention. In the latter (macroscopic) approach, instead, the basic wave equation is not the starting point. It deals directly with the transport of energy through the particulate composite, arriving to a basic differential equation (the equation of transfer). A basic assumption is that there is no correlation between the coexisting scattered fields and, therefore, their intensities can be added directly (as opposed to vectorially adding the fields). A crucial magnitude is the composite depth (particle concentration by number times total cross-section of a single particle times path length). The solution of the equation of transfer depends upon this depth and the so-called phase function. The theory is heuristic as opposed to fundamental and, ergo, it lacks the mathematical rigor and ample validity range of a first-principle approach. As it would be expected, this approach is simpler and more tractable from the numerical point of view. It has flourished during the last 100 years, in great part, due to the lack of sufficient cost-effective computational power to implement the fundamental approach. Nowadays, duplication of computer power every year or so at lower costs, has made it possible to consider full numerical implementation of the fundamental approach using non-expensive computer hardware.

Scientific literature on the analytical multiple-scattering theory is abundant but dispersed throughout a myriad of publications. Main authors who have significantly contributed in the last fifty years are L. L. Foldy, M. Lax, P. C. Waterman and R. Truell, V. Twersky, P. Lloyd and M. V. Berry, J. G. Fikioris and P. C. Waterman, A. K. Mal and S. K. Bose, N. C. Mathur and K. C. Yeh, V. N. Bringi, V. V. Varadan, V. K. Varadan, Y. Ma, L. M. Schwartz, A. J. Devaney, L. Tsang and J. A. Kong, D. D. Phanord and N. E. Berger, de Daran, F. et al, etc. Work of these researchers and others are listed in this patent. The great majority of these publications are dedicated to specific problems in specific fields of applications. A very few, however, recognizing the common underlying structural physico-mathematical core in all these fields, have attempted to formulate generic equations for the prediction of either acoustical, electromagnetic, or elastic waves in particulate composites. The publication [37] "Multiple Scattering Theory for Acoustic, Electromagnetic, and Elastic Waves in Discrete Random Media" by V.V. Varadan, V.K. Varadan and Y. Ma (Multiple Scattering of Waves in Random Media and Random Rough Surfaces, The Pennsylvania State University, 1985) belongs to this kind of general work and constitutes direct theoretical prior-art to this invention as far as the Prediction Engine 21 is concerned (FIG. 1). Even though the approach described in this prior-art and several others has a common theoretical background with the Prediction Engine 21, the latter constitutes a step forward in generality and accuracy, as the present specification will thoroughly demonstrate.

There is finally a third approach in dealing with the multiple-scattering phenomenon that is more limited in scope: it consists basically in attempting to suppress it by conceiving ad-hoc hardware designs and/or software schemes through which the multiple-scattered signal is either significantly attenuated in favor of the single-scattering component, or cross-correlation techniques are employed to filter one component from the other. U.S. Pat. Nos. 6,100,976, 5,956,139, and 4,380,817 belong to this group. This approach is mentioned here for the sake of completeness even though, since no attempt to mathematically modeling multiple-scattering phenomena is made, these patents do not truly constitute prior art to the present invention.

Two important technical fields where the present invention meets a long-term need are those of particle sizing using light scattering and acoustic spectroscopy. This is simply because, in order to indirectly measure a certain constituent attribute (e.g. particle size distribution) with a wave-based instrument, it is strictly necessary to be able to predict —as a function of this constituent attribute-that composite attribute that is directly being measured (e.g. scattering, attenuation, intensity). During the last 30 years or so, measuring of particle size in suspensions, emulsions, and aerosols using the scattering of light have developed to its mature state with a plethora of commercial instruments available in the market. Nonetheless, in practically all of those instruments a sine qua non condition for accurate performance is that the particle concentration should be reduced before analysis to extremely low values (typically under 0.1% v/v)—when actual industrial concentrations are several orders of magnitude higher. One of the main reasons for such an operating constraint is that the mathematical model (e.g. Mie theory) internally employed by these light-scattering instruments is a single-scattering model, i.e. a model that can predict accurately the composite attributes only when the particles are well-separated between each other, so that no interaction between contiguous electromagnetic fields occurs. Multiple scattering is simply not modeled.

A light-scattering instrument for aerosols (host medium is gaseous) that can work at higher concentrations (light transmissions down to 2% as opposed to typical values of about 60% to 80% in other instruments) is the one described by Harvill, T. L. and Holve, D. J. in U.S. Pat. No. 5,619,324, issued Apr. 8, 1997, in which correction for multiple scattering phenomena is conducted through a suitable adaptation of the theory described by E. D. Hirleman in [40] "Modeling of Multiple Scattering Effects in Fraunhofer Diffraction Particle Size Analysis", Particle Characterization 5, 57-65 (1988), and [41] "A General Solution to the Inverse Near-Forward Scattering Particle Sizing Problem in Multiple Scattering Environments: Theory", Proceedings of the $2^{nd}$ International Congress on Optical Particle Sizing, Mar. 5-8 1990, pp. 159-168. With such a correction, this instrument extended the concentration range by a factor of 5-10 (only up to about a few percent by volume). Hirleman's model was developed for the specific case of small-angle scattering with the assumption that scattered fields add incoherently (on an intensity rather than amplitude basis). A "black box" approach is employed through defining a multiple-scattering redistribution matrix that represents how optical energy incident in a certain direction is redistributed by the whole composite into another direction. This matrix not only depends on the nature of medium and particles with their size distribution and concentration, but also on the geometry of the instrument as well as the optical depth of the particulate system. In plain words, the matrix can only be determined (ad hoc) once the instrument (hardware) at hand is known. Hirleman uses also a "successive orders of scattering" approach to express the multiple-scattering matrix in terms of the single-scattering one. Both matrices are global characterizations of the particulate system. No fundamental modeling of the interaction of the wave with a single particle and interaction between scattered waves around particles is undertaken. By further assuming that a scattering event of order n can be represented by the n-power of the single-scattering matrix applied to the incident signal and summing all contributions, Hirleman arrives to an analytical relation between the single and multiple-scattering matrices. The black-box approach plus the dependence of the matrix upon geometry and extension of the medium gives the model a phenomenological character as opposed to a fundamental (first principles) approach. The narrow applicability of a phenomenological approach is therefore in effect.

In U.S. Pat. No. 5,818,583, issued Oct. 6, 1998, E. Sevick-Muraca et al describe a method that applies the so-called diffusion model of light propagation to predict some aspects of multiple scattering of electromagnetic waves with suspensions (host medium is a fluid). When the particle concentration is larger than about 1%, a further approximation to the Radiative Transfer Theory can be made leading to the Diffusion Approximation Theory ([22] A. Ishimaru, 1978). In this diffusion model, it is assumed that the diffusion intensity is scattered in all directions with an almost uniform angular distribution. In what the inventors describe as photon migration techniques, the light intensity of the source is varied in time and the phase shift of the received signal for a number of different wavelengths is directly measured. The isotropic scattering coefficient is then calculated with the diffusion model and, using this coefficient, the particle size and concentration is determined inverting an integral equation that relates the particle size distribution with the scattering coefficient. Due to the diffusion regime assumption, the model cannot be used at low concentration, because the presence of substantial multiple scattering is a necessity for proper performance. Another limitation is that the referred integral equation relating the scattering coefficient with the size distribution assumes no interaction between particles occurs (the scattering coefficient is proportional to the particle concentration). This equation can only be valid when particles are far apart. As a result, the model will only be accurate when multiple scattering is strong enough for the diffusion approximation to hold but yet the particles being far apart enough so no interaction occurs between them so equation 3 in column 9, line 55 of this prior-art patent can be valid. These are opposite requirements in terms of particle concentration. Consequent with this fact, the experimental data shown in the patent correspond to concentrations around 1%—when actual industrial concentrations are much higher than that. This is specifically discussed by the authors of the patent in [46] "Photon-Migration Measurement of Latex Size Distribution in Concentrated Suspensions", AIChE Journal, March 1997, Vol. 43, No. 3. In addition, due to the assumption of "almost uniform angular distribution of scattering", validity of the model will break down as the ratio between the size of the particles and the wavelength increases. This is because the larger the particle size as compared to the wavelength, the stronger the directivity of the scattering in the forward direction is.

In U.S. Pat. No. 5,121,629, issued Jun. 16, 1992, a method and apparatus are described for measuring particle size distribution that employs a fundamental mathematical model for scattering of ultrasound waves in suspensions or emulsions (host medium is a fluid). The modeling aspects of this prior patent actually constitute the most direct prior-art patent to the current invention as far as its application to predicting the attenuation of acoustic waves in suspensions is concerned. Modeling details in this prior patent start in column 8, line 29 up to column 12, line 46. As in the METAMODEL™ Prediction Engine 21 of the current invention, modeling in this prior patent employs the fundamental wave scattering theory. It starts with the first-principle description of the interaction of a wave with a single particle (the particle/medium signature), and proceeds to statistically formulate the field relations within an ensemble of particles of different sizes. It ends with an analytical equation that relates the propagation constant of the composite with the propagation constant of the host medium, the physical properties of both medium and particles, as well as their size distribution and concentration. There are, however, three essential differences with the current invention when applied to acoustics. Two of them are associated with the particle/medium signature for which this prior-art patent uses the Epstein-Carhart-Allegra-Hawley (ECAH) theory while the present invention adds to this ECAH theory the following: a) modeling for possible viscoelastic behavior of both host medium and particle and b) modeling for phenomena due to surface tension which is important in gaseous particles. The third paramount difference has to do with the overlapping of contiguous fields: the prior patent arrives to equation 8 (column 10, line 60), which is the statistical relation obtained by Waterman and Truell in [9] "Multiple Scattering of Waves", J. Math. Phys. Vol. 2, No. 4, July-August, 1961, as a closed-form dispersion equation for the particulate composite. Such a simple closed-form equation was obtained under the assumption of statistically independent point scatterers. In plain words, the expression "point scatterers" refers to the abstract concept of a particle with no physical dimensions but with the scattering properties of its actual size. It was applied in order to simplify the mathematics and its numerical coding into computer software. As a result, model accuracy deteriorates as the size of the particles and/or frequency increase. Regarding the assumption of statistical independence between scatterers positions, it eventually breaks untrue as concentration increases because of the inevitable spatial correlation between particles. Furthermore, P. Lloyd and M. V. Berry ([17] "Wave propagation through an assembly of spheres IV. Relations between different multiple scattering theories", Proc. Phys. Soc., 1967, Vol. 91), proved there was an error in the referred Waterman and Truell's formula "arising from an artificial stratification of the medium into thin slabs". All the referred drawbacks, though not damaging in many cases as demonstrated with the good results disclosed in this prior patent, would instead definitely contribute to destroy the accuracy of a generic model (valid for waves of any nature) if the broadest range of materials, particle size, concentration, and wave frequencies is aimed at. In fact, it will be demonstrated when the Prediction Engine 21 is described in detail that, if scatterers are treated as what they are: finite-size inclusions in the host medium, and the spatial correlation between them is not neglected, it is not possible any longer to arrive at a simple closed-form expression for the dispersion equation. Mathematics and computer programming complexities increase considerably—but prediction accuracy and range of applicability improve drastically.

In U.S. Pat. No. 6,109,098, issued Aug. 29, 2000, A. Dukhin and P. Goetz describe a device that combines acoustic and electroacoustic spectrometry to measure particle size distribution and zeta potential for concentrated dispersed systems. Focusing only on the mathematical modeling part of this prior patent, they use a macroscopic phenomenological approach to modeling the interaction between the sound wave and the concentrated suspension (host medium is a fluid). Specifically, they use the so-called "coupled phase" and "cell" models applying the long-wave regime condition, i.e. the particle size has to be much smaller than the sound wavelength. As a result, this mathematical model is only accurate for particles with sizes smaller than 10 µm. In the same patent Dukhin and Goetz state that the fundamental multiple-scattering approach "is not adequate because even the multiple scattering approach requires a single particle acoustic field which is known only for a single particle in infinite media. . . " The present invention has overcome this difficulty recognized in the prior art conceiving a method based on the fundamental multiple-scattering approach which can work accurately in the particle size range from 1 nanometer to 1 millimeter.

In U.S. Pat. No. 6,119,510, issued Sep. 19, 2000, M. Carasso et al describe an "improved process for determining the characteristics of dispersed particles". The authors contemplate the use of their process with acoustic as well as light waves. Focusing again only in the mathematical modeling, they describe a "computationally improved Allegra-Hawley Model" for acoustics and the original Mie Model for light waves. These two models are single-scattering models and therefore not accurate for high particle concentrations (typically over 10% for acoustics and over 1% for optics). The present invention has overcome this difficulty recognized in the prior art conceiving a method based on the fundamental multiple-scattering approach which can work accurately in the concentration range from 0.001% to 50% by volume.

In summary, there are no research and development tools available for the generic prediction, analysis, and parametric studies of the interaction between generic waves (acoustic, electromagnetic, elastic) and particulate composites. The current invention meets such a long-term need by providing a powerful research and development tool that makes all theoretical physics and numerical intricacies transparent to the human operator. A fundamental mathematical model is a key component of such a tool. The lack of a complete fundamental mathematical model for the prediction of multiple scattering of waves in particulates has, in addition, limited the concentration range of currently existing wave-based instruments. All such instruments which operation is based on the interaction of any type of wave traveling through suspensions, emulsions or solids containing inclusions, could benefit considerably from the prediction engine of this invention. Because the METAMODEL™ Prediction Engine 21 is a separate module connected to the other modules of this invention through industry-standard interfaces, it can be directly integrated to those -already existing- instruments extending their concentration ranges by several orders of magnitude. Further objects and advantages of the present invention will become apparent from a consideration of the ensuing description.

SUMMARY OF THE INVENTION

This invention comprises of three crucial components (FIG. 1): a) a fundamental mathematical model, with its corresponding numerical algorithms to predict the composite physical attributes from the physical attributes of the constituent phases. It is called the METAMODEL™ Prediction Engine 21, b) a set of optimization algorithms to numerically invert the aforesaid mathematical model so as to estimate a subset of the attributes of the constituent phases and composite from the knowledge of the rest of the attributes of the constituent phases and composite. It is called the METAMODEL™ Inversion Engine 22; and c) an ergonomic graphical interface between the prediction and inversion engines and the final user so he/she can easily set up complex simulation experiments to assist in parametric studies, analysis, and synthesis of real systems in which waves of any nature interact with composites. I call this It is called the SCATTERER™ Graphical Interface 23. The Prediction Engine 21 uses a fundamental approach that considers the composite as a random medium and consequently describes it statistically as indicated in block 24 of FIG. 2. The particle/host medium signature is deterministically modeled from the knowledge of the physical properties of particle and host medium and the physics associated with the nature of the problem (acoustical, electromagnetic, elastic) as expressed in block 25. Particle spatial and attribute correlations are modeled as indicated in block 26. Stochastic field equations, assuming a particle is fixed in space with its physical attributes known, are established as represented in block 27. Further averaging over the physical attributes of the fixed particle is performed as expressed in block 28, arriving to the dispersion equations that are solved to determine the propagation constant of the random medium as indicated in block 29. All physical attributes of the composite are thus determined from the composite propagation constant and the physical attributes of the constituent phases as depicted in block 30. The graphical interface 23 is implemented following de facto industry standards for graphical user interfaces. Hierarchies of windows, icons, options and command buttons, checkbox controls, context menus, image controls, tool-tips, on-line help and the like are used to produce an ergonomic efficient interaction between this invention and the human operator. A general-purpose computer 19 and data-carrier media 20 are needed for the full operability of the invention.

DETAILED DESCRIPTION/OPERATION OF THE INVENTION

Detailed Description/Operation of the METAMODEL™ Engines 21 and 22

Figure 1:
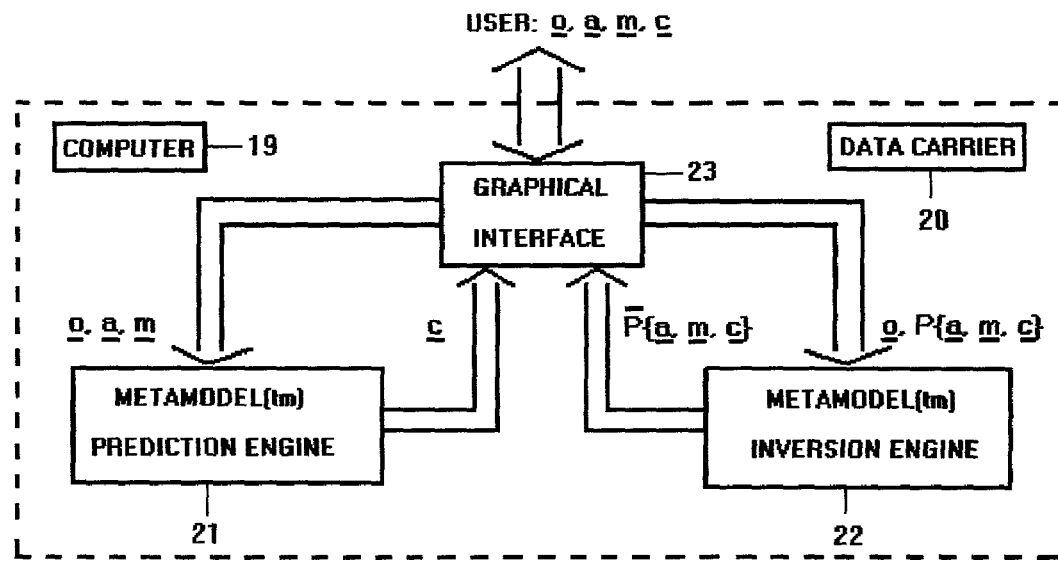
FIG. 1 schematically depicts main components of the invention with their structural relationship.

An essential part of this invention is a generic fundamental mathematical model to predict the interaction between a generic wave (acoustic, electromagnetic, elastic) and a dense generic particulate system (fluid or solid particles included in fluid or solid media). Two numerical engines operate around this mathematical model. The Prediction Engine 21 starts with the operating attribute vector o, the attribute vector m of the host medium, and the attribute vector a of the particles to predict the attribute vector c of the composite (FIG. 1). Vector o contains operating parameters like frequency, temperature, scattering angle, etc. Vector m contains all the physical properties for the suspending medium. Vector a comprises of all the physical properties for the material of the particles plus the particle size distribution and concentration. Some of these properties can be frequency-dependent (e.g. for non-Newtonian fluid or viscoelastic solids, or the refractive index in the optical case). Properties may also be temperature-dependent. The components of vector c are the physical attributes of the composite (attenuation, velocity, intensity, phase shift, elastic constants, etc.). These attributes are in general functions of frequency, temperature, scattering angle, etc. As a clarifying example, for the acoustic case treated in U.S. Pat. No. 5,121,629 the knowledge of the seven disclosed physical properties for both the suspending medium and suspended particles plus the particle size distribution and particle concentration, made it possible to uniquely predict the attenuation coefficient of the ultrasound wave as a function of frequency. The Inversion Engine 22 handles the inverse problem, i.e. knowing some of the attributes of the composite and constituents, it estimates the values of the missing attributes of the constituents and composite (FIG. 1). The symbol P{.} stands for a subset of all properties (the partial knowledge set). The symbol $\overline{P}${.} stands for the missing subset (set complement). As a concrete example, most of the referred patents describe particle size analyzers, viz. instruments that estimate the particle size distribution (a constituent attribute) from the measurement of a composite attribute (attenuation spectrum for U.S. Pat. No. 5,121,629 and U.S. Pat. No. 6,109,098, light intensity as a function of angle for U.S. Pat. No. 5,619,324, and phase shift as a function of wavelength for U.S. Pat. No. 5,818,583) and the knowledge of the rest of the attributes. All the inherent numerical intricacies associated with the inversion of integral equations are well known by those skilled in the art. Non-linear optimization algorithms using Powell or related techniques in multi-dimensional space (W. H. Press et al, "Numerical Recipes, The Art of Scientific Computing", Chapter 10, Cambridge Press, 1988) are routinely employed by those skilled in the art. The present invention-solves the natural extension of the mathematical problem defined by equation [18] in U.S. Pat. No. 5.121,629 so as to provide for a generalized direct/invert algorithmic scheme enabling the human operator to manipulate the mathematical model in any desired direction specifying those parameters that are known as well as those that are not known and are to be estimated. As an example, the engineer/scientist could set up the current invention to use measured attenuation spectral data, particle size, and concentration as inputs to estimate the elastic constants of the particles.

In the preferred embodiment for this invention, incorporated by reference as a computer program listing appendix, both numerical engines 21 and 22 are programmed in Compaq Visual FORTRAN as a Dynamically Linked Library (DLL) called by the Graphical Interface 23 that is programmed in Microsoft Visual Basic® for Windows. Any other language or combination of languages interacting with a different linking technology, e.g. Component Object Model (COM) server technology, could obviously be used to embody the current invention.

The generic mathematical modeling process starts considering a random spatial distribution of $N \to \infty$ particles (scatterers) with arbitrary physical attributes (thermodynamical, size, shape, orientation, acoustic, elastic, electromagnetic, transport, etc.) suspended or included in an otherwise continuous medium with an arbitrary concentration. The particular position and attributes of each scatterer are unknown but the ensemble of them can be statistically described through a probability density function $p(\underline{r}_1, \ldots, \underline{r}_i, \ldots, \underline{r}_N; \underline{a}_1, \ldots, \underline{a}_i, \ldots, \underline{a}_N)$. The symbols $\underline{r}_i$ and $\underline{a}_i$ represent the position and attribute vectors for particle i respectively.

In plain words: $p(\underline{r}_1, \ldots, \underline{r}_i, \ldots \underline{r}_N; \underline{a}_1, \ldots, \underline{a}_i, \ldots, \underline{a}_N) dv_1 \ldots dv_i \ldots dv_N d\underline{a}_1 \ldots d\underline{a}_i \ldots d\underline{a}_N$ is the joint probability of finding one scatterer in the volume $dv_1$ (centered at $\underline{r}_1$) with attribute vector in the neighborhood of $\underline{a}_1$ ($|\underline{a}-\underline{a}_1|\leq\epsilon$), another scatterer in $dv_2$ with attribute vector in the neighborhood of $\underline{a}_2$, etc. The symbol $dv_i$ stands for the volume differential element in $R^3$ with R being the set of real numbers. Calling nA the number of attributes for each particle, note that the symbol $d\underline{a}_i$ stands not for the differential of the vector $\underline{a}_i$, but for the hyper-volume differential element in $R^{nA}$. One of the components of $\underline{a}_i$ is the size of particle i that will be denoted as $d_i$. The simplest practical case commonly considered in the prior multiple-scattering literature is that in which attributes of all scatterers are identical. A few authors considered as well the case in which there is a distribution of sizes throughout the particle population.

A generic wave incites the above random medium. As it is well known from the prior art, assuming the particle concentration is low enough, the local exciting wave at each scattering center can be considered to be simply the global incident wave. This is the well-known single-scattering regime where the behavior of the ensemble is simply proportional to the behavior of the individual particles and the number of them per unit volume. For the acoustical case, this incident wave is normally a longitudinal wave (compressional), i.e., its displacement vector is parallel to the direction of propagation of the wave. At each scattering center this longitudinal wave converts into multiple modes inside as well as outside the particle: two compressional waves (refracted and reflected), two thermal longitudinal waves (inside and outside), and two viscous-inertial transversal waves (inside and outside). At low concentrations these new modes extinguish in the close neighborhood of each particle before interacting with other particles. As the concentration increases, these local waves around the particles overlap and multiple-scattering effects become significant. The detected wave at the receiver is the remaining propagating compressional mode. For the electromagnetic case, the incident wave is transversal, i.e., the plane of vibration of the electrical and magnetic fields is perpendicular to the direction of propagation of the wave. There are normally no conversion modes at each scatterer. The elastodynamic case is the most complex of all, as its vectorial nature is present in both the incident wave as well as in the scattering process that occurs at each particle. The incident wave can have both longitudinal and transversal components and each one of them converts—at each scattering center—into longitudinal and transversal modes.

The incident field is assumed to be that of a monochromatic wave without loss of generality. The factor $e^{-j\omega}$ is consequently implicit in all equations. Except for the incident field, all fields in the particulate system depend upon the spatial/attribute configuration of scatterers $\{\underline{r}_1, \ldots, \underline{r}_i, \ldots, \underline{r}_N; \underline{a}_i, \ldots, \underline{a}_N\}$. This lengthy notation will be maintained throughout the present description for the sake of an enabling disclosure. Referring to the incident field at observation point $\underline{r}$ by $\underline{I}(\underline{r})$, and the field that excites particle i (located at point $\underline{r}_i$ with attribute vector $\underline{a}_i$) at observation point $\underline{r}$ by $\underline{E}(\underline{r}/\underline{r}_i;\underline{a}_i: \{\underline{r}_1, \ldots \underline{r}_i, \ldots, \underline{r}_N; \underline{a}_1, \ldots, \underline{a}_i, \ldots, \underline{a}_N\})$. Similarly, calling the field scattered by particle j (located at $\underline{r}_j$ with attribute $\underline{a}_j$) when particle i with attribute $\underline{a}_i$ is located at $r_i$ by $\underline{S}(r/r_j, r_i; \underline{a}_j, \underline{a}_i: \{r_1, \ldots, r_i, \ldots, r_j, \ldots, r_N; \underline{a}_1, \ldots, \underline{a}_i, \underline{a}_j, \ldots, \underline{a}_N\})$, the following important generic equation is valid:

$$\underline{E}(r/r_i; \underline{a}_i: \{r_1, \ldots, r_i, \ldots, r_N; \underline{a}_1, \ldots, \underline{a}_i, \ldots, \underline{a}_N\}) = \quad (1)$$

$$I(r) + \sum_{j=1, j\neq i}^{N} \underline{S}(r/r_j r_i; \underline{a}_j \underline{a}_i: \{r_1, \ldots, r_i, \ldots, r_j, \ldots, r_N; \underline{a}_1, \ldots, \underline{a}_i, \ldots, \underline{a}_j, \ldots, \underline{a}_N\})$$

Following Foldy's [2] approach to handle the statistical nature of the physical system under consideration, the expected (average) value of a field at the observation point $\underline{r}$ is defined as the configurational average over all possible spatial/attribute distributions of the scatterers:

$$\langle \underline{E}(r) \rangle = \quad (2)$$

$$\int_V \cdots \int_V \int_D \cdots \int_D \underline{F}(r: \{r_1, \ldots, r_i, \ldots, r_N; \underline{a}_1, \ldots, \underline{a}_i, \ldots \underline{a}_N\}) p(r_1, \ldots, r_i, \ldots r_N; \underline{a}_1, \ldots, \underline{a}_i, \ldots, \underline{a}_N) dv_1 \ldots dv_i$$

$$\ldots dv_N d\underline{a}_1 \ldots d\underline{a}_i \ldots d\underline{a}_N \quad \forall \underline{F} \in \{\underline{I}, \underline{E}, \underline{S}\}$$

The domain of integration V is the volume accessible to the scatterers, i.e., a subset of $R^3$. The domain D of the attributes is a subset of $R^{nA}$. Because of the random nature of the system all fields can be thus expressed as:

$$\underline{E}(r) = \langle \underline{E}(r) \rangle + \underline{E}_1(r) \quad (3)$$

Symbols $\langle \underline{E}(r) \rangle$ and $\underline{E}_1(r)$ represent the coherent and incoherent fields respectively. The incoherent field is the truly random part of the total field. Through the introduction of conditional probabilities, the expected value of a field observed at $\underline{r}$ when a particle is assumed to be at $\underline{r}_i$ with attribute vector $\underline{a}_i$ (first order conditional average) is:

$$\langle \underline{F}(r/r_i; \underline{a}_i) \rangle = \quad (4)$$

$$\int_{V_i} \cdots' \cdots \int_{V_i} \int_D \cdots' \cdots \int_D \underline{F}(r/r_i; \underline{a}_i: \{r_1, \ldots, r_i, \ldots, r_N; \underline{a}_1, \ldots, \underline{a}_i, \ldots, \underline{a}_N\}) p(r_1, \ldots, ' \ldots r_N; \underline{a}_1, \ldots, ', \ldots, \underline{a}_N/r_i; \underline{a}_i) dv_1 \ldots'$$

$$\ldots dv_N d\underline{a}_1 \ldots' \ldots d\underline{a}_N \quad \forall \underline{F} \in \{\underline{I}, \underline{E}, \underline{S}\}$$

The primes in the previous formula mean that $\underline{r}_i$ and $\underline{a}_i$ are not varied throughout the averaging process as clearly expressed by the conditional probability. The domain of integration Vi is V minus a sphere of diameter $d_i$. For the case of assuming particles i and j respectively at locations $\underline{r}_i$ and $\underline{r}_j$ with properties $\underline{a}_i$ and $\underline{a}_j$ (second order conditional average) it is obtained:

$$\langle \underline{F}(r/r_i, r_j; \underline{a}_i, \underline{a}_j) \rangle = \quad (5)$$

$$\int_{V_{ij}} \cdots' \cdots \int_{V_{ij}} \int_D \cdots' \cdots \int_D \underline{F}(r/r_i, r_j; \underline{a}_i, \underline{a}_j):$$

-continued $$\{r_1, \ldots, r_i, \ldots, r_j, \ldots r_N; \underline{a}_1, \ldots, \underline{a}_i, \ldots, \underline{a}_j, \ldots, \underline{a}_N\})$$

$$p(r_1, \ldots, ', \ldots, ', \ldots r_N; \underline{a}_1, \ldots, ', \ldots, ', \ldots, \underline{a}_N/r_i, r_j; \underline{a}_i, \underline{a}_j)$$

$$dv_1 \ldots' \ldots' \ldots dv_N d\underline{a}_1 \ldots'$$

$$\ldots' \ldots d\underline{a}_N \quad \forall \underline{F} \in \{\underline{I}, \underline{E}, \underline{S}\}$$

Without further explanation, statistics of higher order are straightforwardly defined. The global configurational average $\langle \underline{F}(r) \rangle$ can then be expressed in terms of the first partial average as follows:

$$\langle \underline{F}(r) \rangle = \int_V \int_D \langle \underline{F}(r/r_i; \underline{a}_i) \rangle p(r_i; \underline{a}_i) d\underline{a}_i dv_i \quad \forall \underline{F} \in \{\underline{I}, \underline{E}, \underline{S}\} \quad (6)$$

Similarly, the first partial average can be expressed in terms of the second as:

$$\langle \underline{F}(r/r_i; \underline{a}_i) \rangle = \quad (7)$$

$$\int_{V_i} \int_D \langle \underline{F}(r/r_i, r_j; \underline{a}_i, \underline{a}_j) \rangle p(r_j; \underline{a}_j/r_i; \underline{a}_i) d\underline{a}_j dv_j =$$

$$\int_{V_i} \int_D \langle \underline{F}(r/r_j; \underline{a}_j) \rangle p(r_j; \underline{a}_j/r_i; \underline{a}_i)$$

$$d\underline{a}_j dv_j \quad \forall \underline{F} \in \{\underline{I}, \underline{E}, \underline{S}\}$$

In general then, the partial average of order k can be expressed in terms of the partial average of order k+1 and the corresponding conditional probability. Pursuing this recurrence throughout the whole population is obviously impractical. In order to break the recurrence, it is used in the above second equality a generalization of the so-called "quasi-crystalline" approximation introduced first by Lax [3,4]. It consists in assuming that $\langle \underline{F}(r/r_i, r_j; \underline{a}_i, \underline{a}_j) \rangle = \langle \underline{F}(r/r_j; \underline{a}_j) \rangle$. Breaking the recurrence at a higher statistical level is also contemplated in this invention but it would complicate considerably more the mathematical modeling process as well as its disclosure in this specification with no significant practical advantage.

Taking now the configurational average of both terms in equation 1 and using equation 7, it is thus obtained:

$$\langle \underline{E}(r/r_i; \underline{a}_i) \rangle = \quad (8)$$

$$I(r) + \sum_{j=1, j\neq i}^{N} \int_{V_i} \int_D \langle \underline{S}(r/r_j; \underline{a}_j) \rangle p(r_j; \underline{a}_j/r_i; \underline{a}_i) d\underline{a}_j dv_j$$

Let us now define $n(\underline{r}_j, \underline{a}_j) d\underline{a}_j dv_j$ as the number of scatterers in the neighborhood of point $\underline{r}_j$ and with attribute vector $\underline{a}$ in the neighborhood of $\underline{a}_j$. Let us further define $p(\underline{r}_j; \underline{a}_j) d\underline{a}_j dv_j = n(\underline{r}_j, \underline{a}_j) d\underline{a}_j dv_j/N$, i.e., the ratio between the number of particles with attribute in the neighborhood of $\underline{a}_j$ and location in the neighborhood of $\underline{r}_j$, and the total number of particles in the ensemble. Assuming there is no global correlation between position and attribute, it is possible to simplify the joint probability as $p(\underline{r}_j; \underline{a}_j) = n(\underline{r}_j) n(\underline{a}_j)/N^2 = n(\underline{r}_j) f_n(\underline{a}_j)/N$. We have introduced the function $f_n(\underline{a}_j)$ as the density distribution by number for the attributes of particle j in the neighborhood of $\underline{r}_j$. When the attribute is particle size, $f_n(\underline{a}_j)$ is the standard particle size distribution by number but local to the neighborhood of $r_j$. The non-segregation assumption also implies $f_n(a_j)=f_n(a_i)=f_n(a)$ which is now the standard ensemble particle size distribution. Along similar intuitive lines, the conditional probability can be defined as:

$$p(r_j; a_j/r_i; a_i) = \{n(r_j, a_j)/(N(N-1))\} g(r_j, a_j, r_i, a_i) \quad (9)$$

The function $g(r_j, a_j, r_i, a_i)$ is a measure of the local correlation between the positions and attributes of the particles. It basically depends on the nature and range of the interparticle forces. A very successful approximation commonly used in statistical mechanics (the so-called Pair Correlation Function) consists in assuming particles are impenetrable and that the correlation is only a function of their distance $r=|r_j-r_i|$ and the sum of their radii $D=(d_j+d_i)/2$:

$$g(r_j, a_j, r_i, a_i) = g(r; D) = H(r-D) CF(r) \quad (10)$$

The function $H(x)$ is the Heaviside step function which value is 0 for $x<0$ and 1 for $x \geq 0$. When $CF(r)=1$ it is the simplest approximation to correlation: as long as particles do not interpenetrate, given that particle i is located at $r_i$, the chance of particle j to be located at $r_j$ with attribute $a_j$ is governed exclusively by $p(r_j; a_j)$. This is called the "hole correction" in the prior art [13]. In general, the function $CF(r)$ is oscillatory approaching unity as the distance between the two particles increases simply because as two particles separate away, their spatial correlation disappear. There is an extended literature regarding the calculation of $CF(r)$. The most successful and well-known form is the so-called Percus-Yevick approximation from the theory of classical fluids. Other approaches are the so-called hyper-netted chain equation, the Virial expansion, the self-consistent approximation, etc. A powerful technique recently developed is based on Monte-Carlo simulation of a large number of scatterer spatial configurations. The current invention, in its graphical user interface, provides for most of these well-known forms for $CF(r)$ as set-up options. Another powerful option provided by this invention is to allow for this oscillatory function to be characterized by three parameters (amplitude, frequency, and decay) and let the user experiment with them in trying to accurately modeling the unique spatial correlation characteristics of the problem at hand. The following relation is then valid:

$$\langle E(r/r_i; a_i) \rangle = \quad (11)$$

$$I(r) + \int_{V_i} \int_D \langle S(r/r_j; a_j) \rangle n(r_j, a_j) g(r_j, a_j, r_i, a_i) da_j dv_j$$

Figure 2:
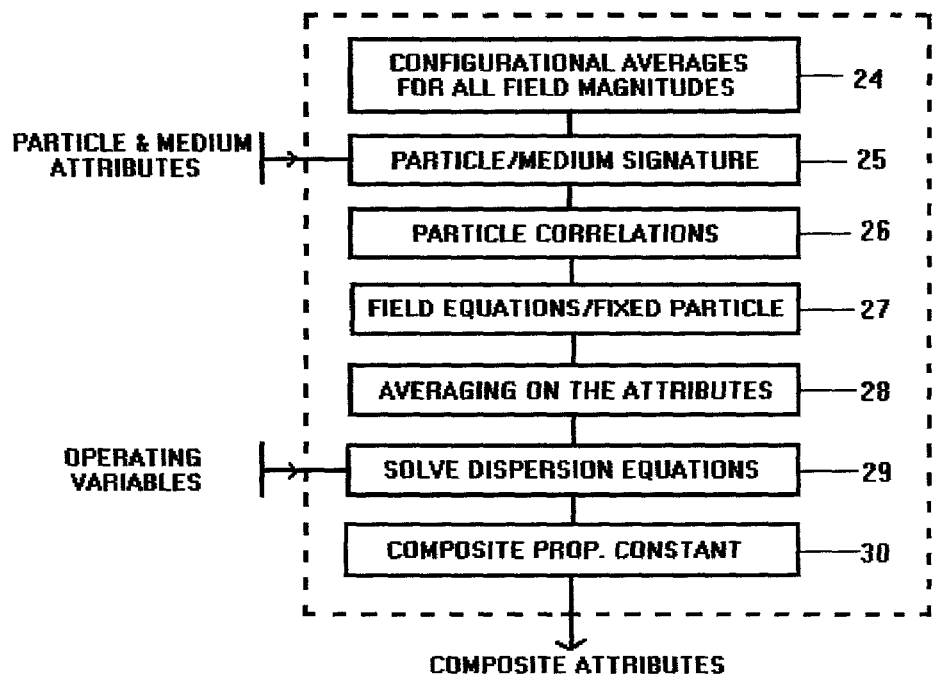
FIG. 2 schematically displays main modeling steps in the METAMODEL™ Prediction Engine.

Referring to FIG. 2, prior equations 1 through 8 disclose the implementation of block 24 while equations 9 through 11 disclose the implementation of block 26. As for the disclosure of block 25, the field scattered by a single particle has been separately studied in the prior literature for all acoustic, electromagnetic, and elastic cases. The most general form of expressing the scattered field generated by scatterer j due to its exciting field is through the so-called transition matrix operator as follows:

$$S(r/r_j; a_j; \{r_1, \ldots, r_j, \ldots r_N; a_1, \ldots, a_j, \ldots, a_N\}) = \underline{T}(\underline{o}, \underline{m}, a_j) E(r/r_j; a_j; \{r_1, \ldots, r_j, \ldots, r_N; a_1, \ldots, a_j, a_N\}) \quad (12)$$

In plain words, the transition matrix constitutes a behavioral signature for the basic individual interaction between the wave and a single particle suspended in the medium. It is called the particle/medium signature. Notice that both the exciting and scattered fields depend upon the spatial/attribute configuration of scatterers, while the transition operator only depends upon the host medium properties, the particle j properties, the operating parameters (frequency, temperature, etc) and the nature of the incident physical wave (acoustic, electromagnetic, elastic). It is a representation of the Green's function for a single scatterer in the host medium (single scattering problem). When the incident wave is electromagnetic, this invention employs the well-known Mie-Scattering model to define the transition operator. In the acoustic case the transition operator is obtained from: 1) [5] P. S Epstein and R. R. Carhart, "The Absorption of Sound in Suspensions and Emulsions, I. Water Fog in Air", J. Acoust. Soc. Am., 25 [3] 553-565 (1953), 2) A correction to the thermal diffusion effect due to surface tension is included from the work of J. C. F. Chow, [14] "Attenuation of Acoustic Waves in Dilute Emulsions and Suspensions", J. Acoust. Soc. Am., 36 [12] 2395-2401 (1964), 3) A more complete treatment for both solid and fluid particles is taken from J. R. Allegra and S. A. Hawley, [19] "Attenuation of Sound in Suspensions and Emulsions: Theory and Experiments", J. Acoust. Soc. Am., 51, 1545-1564 (1972), and 4) Viscoelastic behavior of both particles and host medium is modeled along the lines described in C. Verdier and M. Piau, [47] "Acoustic Wave Propagation in Two-phase viscoelastic fluids: The Case of Polymer emulsions", J. Acoust. Soc. Am. 101[4], 1868-1876, April 1997 and J. Y. Kim et al, [44] "Dispersive Wave Propagation in a Viscoelastic Matrix Reinforced by Elastic Fibers", J. Acoust. Soc. Am., 95 (3), March 1994. The transition operator for elastic waves is obtained through a combination of the treatment described for the acoustic case and the approach described in 1) N. G. Einspruch and R. Truell, [7] "Scattering of a Plane Longitudinal Wave by a Spherical Fluid Obstacle in an Elastic Medium", J. Acoust. Soc. Am., 32 [2], 214-220, February 1960, and 2) N. G. Einspruch et al, [8] "Scattering of a Plane Transverse Wave by a Sherical Obstacle in an Elastic Medium", J. Appl. Phys., 31 [5], 806-817, May 1960.

In terms of this basic signature and equation 11, the global behavior of the ensemble (multiple scattering) will be predicted. Taking the configurational average on both sides of equation 12 it is obtained:

$$\langle S(r/r_j; a_j) \rangle = \underline{T}(\underline{o}, \underline{m}, a_j) \langle E(r/r_j; a_j) \rangle \quad (13)$$

Replacing equation 13 in equation 11 the following important relation is valid:

$$\langle E(r/r_i; a_i) \rangle = I(r) + \int_{V_i} \int_D \underline{T}(\underline{o}, \underline{m}, a_j) \quad (14)$$

$$\langle E(r/r_j; a_j) \rangle n(r_j, a_j) g(r_j, a_j, r_i, a_i) da_j dv_j$$

Given a fixed spatial/attribute distribution of scatterers, all fields (external and internal to the particles) are supposed to verify the Helmholtz's vector wave equation:

$$(\nabla^2+k^2) \underline{E}(r; \{r_1, \ldots, r_i, \ldots, r_N; a_1, \ldots, a_i, \ldots, a_N\}) = 0 \quad \forall \underline{E} \in \{I, E, S\} \quad (15)$$

The symbol $\nabla^2$ stands for the Laplacian of a vectorial field and k is the wave number for the particular field. The general solution to this equation may be expressed as a linear combination of three independent discrete sets of vector solutions $\{\underline{L}_{nm}\}$ (longitudinal), $\{\underline{M}_{nm}\}$ (transversal) and $\{\underline{N}_{nm}\}$ (transversal) with arbitrary constants $\{f_{nm1}, f_{nm2}, f_{nm3}\}$ as follows [1]:

$$\underline{F}(\underline{r}) = \sum_{n=0}^{\infty} \sum_{m=-n}^{m=n} [f_{nm1}\underline{L}_{nm}(\underline{r}) + f_{nm2}\underline{M}_{nm}(\underline{r}) + f_{nm3}\underline{N}_{nm}(\underline{r})] \quad (16)$$

$$\forall \underline{F} \in \{I, E, S\}$$

Purely irrotational fields could be expressed exclusively in terms of the $\{\underline{L}_{nm}\}$ eigenvectors; purely solenoidal fields could be expressed exclusively in terms of both $\{\underline{M}_{nm}\}$ and $\{\underline{N}_{nm}\}$ eigenvectors. All three types of basis vector functions are directed related to the discrete set of solutions $\{\Psi_{nm}(\underline{r})\}$ for the corresponding scalar Helmholtz wave equation [1]. For particles with shapes randomly deviating from the spherical shape, spherical coordinates are appropriate. For fiber-shaped particles, cylindrical coordinates are the suitable choice. For the sake of continuing the disclosure, using spherical coordinates $(r, \theta, \phi)$, the associated discrete sets $\{\underline{L}_{nm}\}, \{\underline{M}_{nm}\}, \{\underline{N}_{nm}\}$ are:

$$\Psi_{nm}(\underline{r}) = \Psi_{nm}(r, \theta, \phi) = P_n^m(\cos\theta) \cdot z_n(kr) \cdot e^{im\phi} \forall n \in \{0, 1, \ldots, \infty\}; \forall m \in \{-n, \ldots 0 \ldots n\}$$

$$\underline{L}_{nm} = \nabla \Psi_{nm} \quad \underline{M}_{nm} = \nabla \times \underline{r} \Psi_{nm} = \underline{L}_{nm} \times \underline{r} \quad \underline{N}_{nm} = (1/k) \nabla \times \underline{M}_{nm} \quad (17)$$

The $\{P_n^m(\cos\theta)\}$ set comprises of the well known associated Legendre Polynomials; and the $\{z_n\}$ set is either the set of spherical Bessel functions $\{j_n\}$ or the set of Hankel functions $\{h_n\}$ The Bessel set is chosen for those fields that are to be regular at the origin (incident field and the internal field of a particle); the Hankel functional set is used for those fields that are to verify the radiation condition at infinity (the scattered fields). Superscripts B or H will be added to $\{\underline{L}_{nm}\}, \{\underline{M}_{nm}\}, \{\underline{N}_{nm}\}$ according to the case.

Let the symbol Ndw stand for "Number of different waves" occurring during the interaction between the exciting wave and the particle. For instance, in the acoustic problem, as described in U.S. Pat. No. 5,121,629, Ndw would be equal to 3 with the value 1 corresponding to the compressional waves, value 2 corresponding to the longitudinal thermal waves, and the value 3 corresponding to the viscous transversal waves. Adding then a new subscript $k=1$, Ndw, and defining $k_k$ as the corresponding wave number, the following equalities are valid in spherical coordinates:

$$L_{nmk}(\underline{r}) = \left\{\frac{\partial}{\partial r} z_n(k_k r) P_n^m(\cos\theta) e^{im\phi}\right\} \underline{e}_r + \quad (18)$$

$$\left\{z_n(k_k r) \frac{\partial}{r \partial r} P_n^m(\cos\theta) e^{im\phi}\right\} \underline{e}_\theta +$$

$$\left\{\frac{im}{r\sin\theta} z_n(k_k r) P_n^m(\cos\theta) e^{im\phi}\right\} \underline{e}_\phi$$

$$M_{nmk}(\underline{r}) = \left\{\frac{im}{\sin\theta} z_n(k_k r) P_n^m(\cos\theta) e^{im\phi}\right\} \underline{e}_\theta +$$

$$\left\{z_n(k_k r) \frac{\partial}{\partial \theta} P_n^m(\cos\theta) e^{im\phi}\right\} \underline{e}_\phi$$

$$N_{nmk}(\underline{r}) = \left\{\frac{n(n+1)}{k_k r} z_n(k_k r) P_n^m(\cos\theta) e^{im\phi}\right\} \underline{e}_r +$$

$$\left\{\frac{\partial}{k_k r \partial r} r z_n(k_k r) \frac{\partial}{\partial \theta} P_n^m(\cos\theta) e^{im\phi}\right\} \underline{e}_\theta +$$

$$\left\{\frac{\partial}{k_k r \partial r} r z_n(k_k r) \frac{im}{\sin\theta} P_n^m(\cos\theta) e^{im\phi}\right\} \underline{e}_\phi$$

It is worth noting that equations 5 and 6 of prior art U.S. Pat. No. 5,121,629 are special versions of our generic equation 16 in spherical coordinates (upon use of equation 18) for the simpler acoustic case where the incident wave is purely longitudinal (a field of gradients). Let us now apply our equation 16 to the exciting field surrounding particle i located at position $\underline{r}_i$ as well as to the field scattered by particle j located at position $\underline{r}_j$, and take configurational averages:

$$\langle \underline{E}(\underline{r}/\underline{r}_i; \underline{a}_i) \rangle = \sum_{n=0}^{\infty} \sum_{m=-n}^{m=n} \sum_{k=1}^{Ndw} [\langle e_{nmk1}(\underline{r}_i; \underline{a}_i) \rangle L_{nmk}^B(\underline{r} - \underline{r}_i) + \quad (19)$$

$$\langle e_{nmk2}(\underline{r}_i; \underline{a}_i) \rangle M_{nmk}^B(\underline{r} - \underline{r}_i) +$$

$$\langle e_{nmk3}(\underline{r}_i; \underline{a}_i) \rangle N_{nmk}^B(\underline{r} - \underline{r}_i)]$$

$$\forall \underline{r}: |\underline{r} - \underline{r}_i| \leq b$$

$$\langle \underline{S}(\underline{r}/\underline{r}_j; \underline{a}_j) \rangle = \sum_{n=0}^{\infty} \sum_{m=-n}^{m=n} \sum_{k=1}^{Ndw} [\langle s_{nmk1}(\underline{r}_j; \underline{a}_j) \rangle L_{nmk}^H(\underline{r} - \underline{r}_j) + \quad (20)$$

$$\langle s_{nmk2}(\underline{r}_j; \underline{a}_j) \rangle M_{nmk}^H(\underline{r} - \underline{r}_j) +$$

$$\langle s_{nmk3}(\underline{r}_j; \underline{a}_j) \rangle N_{nmk}^H(\underline{r} - \underline{r}_j)]$$

$$\forall \underline{r}: |\underline{r} - \underline{r}_j| \geq b$$

The symbol b stands for the distance of closest approach between particles i and j $(b \geq (d_i + d_j)/2)$. Following the expansions in equations 19 and 20, applying a suitable set of boundary conditions around particle j, and adding the polarization index $q=1,2,3$, the abstract nature of the operator $\underline{T}(\underline{o}, \underline{m}, \underline{a}_j)$ materializes into a multi-dimensional infinite matrix that relates each scattering coefficient in equation 20 with all the coefficients in equation 19 as:

$$\langle s_{nmkq}(\underline{r}_j; \underline{a}_j) \rangle = \sum_{r=0}^{\infty} \sum_{s=-r}^{s=r} \sum_{t=1}^{Ndw} \sum_{u=1}^{3} T_{rstu}^{nmkq}(\underline{o}, \underline{m}, \underline{a}_j) \langle e_{rstu}(\underline{r}_j; \underline{a}_j) \rangle \quad (21)$$

$$= \sum_{rstu} T_{rstu}^{nmkq}(\underline{o}, \underline{m}, \underline{a}_j) \langle e_{rstu}(\underline{r}_j; \underline{a}_j) \rangle$$

In the electromagnetic case, due to the purely solenoidal character of the wave and the spherical symmetry involved, only $T_{n112}^{n112}(\underline{o}, \underline{m}, \underline{p}_j)$ and $T_{n113}^{n113}(\underline{o}, \underline{m}, \underline{p}_j)$ are needed and they coincide with the well known Mie coefficients $a_n$ and $b_n$ in the prior art [27]. In the acoustic and elastic cases both longitudinal and transversal waves exist. Applying the single summation convention used in equation 21, equation 20 now becomes:

$$\langle \underline{S}(\underline{r}/\underline{r}_j; \underline{a}_j) \rangle = \sum_{nmk} \left[ \left\{ \sum_{rst} T_{rst1}^{nmk1}(\underline{o}, \underline{m}, \underline{a}_j) \langle e_{rst1}(\underline{r}_j; \underline{a}_j) \rangle \right\} \quad (22) \right.$$

$$L_{nmk}^H(\underline{r} - \underline{r}_j) + \sum_{rst} T_{rst2}^{nmk2}(\underline{o}, \underline{m}, \underline{a}_j)$$

$$\langle e_{rst2}(\underline{r}_j; \underline{a}_j) \rangle \} M_{nmk}^H(\underline{r} - \underline{r}_j) +$$

$$\left\{ \sum_{rst} T_{rst3}^{nmk3}(\underline{o}, \underline{m}, \underline{a}_j) \langle e_{rst3}(\underline{r}_j; \underline{a}_j) \rangle \right\}$$

$$\left. N_{nmk}^H(\underline{r} - \underline{r}_j) \right]$$

And, consequently, equation 14 converts to:

$$\sum_{nmk} [\langle e_{nmk1}(\underline{r}_i; \underline{a}_i)\rangle L_{nmk}^B(\underline{r}-\underline{r}_i) + \tag{23}$$

$$\langle e_{nmk2}(\underline{r}_i; \underline{a}_i)\rangle M_{nmk}^B(\underline{r}-\underline{r}_i) + \langle e_{nmk3}(\underline{r}_i; \underline{a}_i)\rangle N_{nmk}^B(\underline{r}-\underline{r}_i)] =$$

$$\sum_{nmk} [i_{nmk1}(\underline{r}_i)L_{nmk}^B(\underline{r}-\underline{r}_i) + i_{nmk2}(\underline{r}_i)M_{nmk}^B(\underline{r}-\underline{r}_i) +$$

$$i_{nmk3}(\underline{r}_i)N_{nmk}^B(\underline{r}-\underline{r}_i)] + \int_{Vi}\int_{Di} n(\underline{r}_j, \underline{a}_j)g(\underline{r}_j, \underline{a}_j, \underline{r}_i, \underline{a}_i)$$

$$\sum_{nmk}\left[\left\{\sum_{rst} T_{rst1}^{nmk1}(\varrho, m, \underline{a}_j)\langle e_{rst1}(\underline{r}_j; \underline{a}_j)\rangle\right\} L_{nmk}^H(\underline{r}-\underline{r}_j) + \right.$$

$$\left\{\sum_{rst} T_{rst2}^{nmk2}(\varrho, m, \underline{a}_j)\langle e_{rst2}(\underline{r}_j; \underline{a}_j)\rangle\right\} M_{nmk}^H(\underline{r}-\underline{r}_j) +$$

$$\left\{\sum_{rst} T_{rst3}^{nmk3}(\varrho, m, \underline{a}_j)\langle e_{rst3}(\underline{r}_j; \underline{a}_j)\rangle\right\}$$

$$\left. N_{nmk}^H(\underline{r}-\underline{r}_j)\right] d\underline{a}_j dv_j$$

In the above equation the eigenvectors are expanded around the location of particle i in both the exciting field and the incident field. However, in the terms associated with the scattered fields, the eigenvectors are expanded around the location of particle j. It is worth noting as well that the latter eigenvectors are expressed in terms of Hankel functions while the former are expressed in terms of Bessel functions. In order to take subsequent advantage of the orthogonality of these vector functions, all of them need to be expressed in terms of the same type of functions and around a single location. For the purpose, it is used the translational addition theorem for spherical vector wave functions well known in the prior literature which can be stated as:

$$L_{nmk}^H(\underline{r}-\underline{r}_j) = \sum_{v=0}^{\infty}\sum_{\mu=-v}^{v} A_{v\mu}^{nmk1}(\underline{r}_j-\underline{r}_i)L_{v\mu k}^B(\underline{r}-\underline{r}_j) \tag{24}$$

$$= \sum_{v\mu} A_{v\mu}^{nmk1}(\underline{r}_j-\underline{r}_i)L_{v\mu k}^B(\underline{r}-\underline{r}_i)$$

$$M_{nmk}^H(\underline{r}-\underline{r}_j) = \sum_{v\mu} A_{v\mu}^{nmk2}(\underline{r}_j-\underline{r}_i)M_{v\mu k}^B(\underline{r}-\underline{r}_i) +$$

$$A_{v\mu}^{nmk3}(\underline{r}_j-\underline{r}_i)N_{v\mu k}^B(\underline{r}-\underline{r}_i)]$$

$$N_{nmk}^H(\underline{r}-\underline{r}_j) = \sum_{v\mu} A_{v\mu}^{nmk3}(\underline{r}_j-\underline{r}_i)M_{v\mu k}^B(\underline{r}-\underline{r}_i) +$$

$$A_{v\mu}^{nmk2}(\underline{r}_j-\underline{r}_i)N_{v\mu k}^B(\underline{r}-\underline{r}_i)]$$

Where the translational coefficients $A_{v\mu}^{nmkq}$ are given by:

$$A_{v\mu}^{nmkq} = \sum_p a_q(n, m, v, \mu, p)h_p(k_k r_{ij})P_p^{m-\mu}(\cos\theta_{ij})\exp(i(m-\mu)\phi_{ij}) \tag{25}$$

The index p varies over the range $|n-v|, |n-v|+2, \ldots n+v$ and the coefficients $a_q(n, m, v, \mu, p)$ are:

$$a_1(n, m, v, \mu, p) = (-1)^\mu i^{v+p-n}(2v+1)a(m, n|-\mu, v|p)$$

$$a_2(n, m, v, \mu, p) = (-1)^\mu i^{v+p-n}a(n, v, p)a(m, n|-\mu, v|p)$$

$$a_3(n, m, v, \mu, p) = (-1)^\mu i^{v+p-n}b(n, v, p)a(m, n|-\mu, v|p, p-1)$$

$$a(n, v, p), b(n, v, p), a(m, n|, -\mu, v|p) \text{ and}$$

$$a(m, n|, -\mu, v|p, p-1) \text{ are:}$$

$$a(n, v, p) = [2v(v+1)(2v+1) + (v+1)(n-v+p+1)(n+v-p) -$$

$$v(v-n+p+1)(n+v+p+2)]/[2v(v+1)]$$

$$b(n, v, p) = [(n+v+p+1)(v-n+p)(n-v+p)(n+v-p+1)]^{1/2}$$

$$(2v+1)/[2v(v+1)]$$

$$a(m, n|, -\mu, v|p) = (-1)^{m+\mu}(2p+1)\left[\frac{(n+m)!(v+\mu)!(p-m-\mu)!}{(n-m)!(v-\mu)!(p+m+\mu)!}\right]^{1/2}$$

$$\left(\begin{array}{ccc}n\ldots v\ldots p\\ m\ldots \mu\ldots -(m+\mu)\end{array}\right)\left(\begin{array}{ccc}n\ldots v\ldots p\\ 0\ldots 0\ldots 0\end{array}\right)$$

$$a(m, n|, -\mu, v|p, q) =$$

$$(-1)^{m+\mu}(2p+1)\left[\frac{(n+m)!(v+\mu)!(p-m-\mu)!}{(n-m)!(v-\mu)!(p+m+\mu)!}\right]^{1/2}$$

$$\left(\begin{array}{ccc}n\ldots v\ldots p\\ m\ldots \mu\ldots -(m+\mu)\end{array}\right)\left(\begin{array}{ccc}n\ldots v\ldots p\\ 0\ldots 0\ldots 0\end{array}\right)$$

The symbol $$\left(\begin{array}{ccc}j_1\ldots j_2\ldots j_3\\ m_1\ldots m_2\ldots -(m_1+m_2)\end{array}\right)$$

is the well-known Wigner 3j symbol [6]. Upon application of equations 24, equation 23 transforms to:

$$\sum_{nmk}[\langle e_{nmk1}(\underline{r}_i; \underline{a}_i)\rangle L_{nmk}^B(\underline{r}-\underline{r}_i) + \langle e_{nmk2}(\underline{r}_i; \underline{a}_i)\rangle M_{nmk}^B(\underline{r}-\underline{r}_i) + \tag{26}$$

$$\langle e_{nmk3}(\underline{r}_i; \underline{a}_i)\rangle N_{nmk}^B(\underline{r}-\underline{r}_i)] =$$

$$\sum_{nmk}[i_{nmk1}(\underline{r}_i)L_{nmk}^B(\underline{r}-\underline{r}_i) + i_{nmk2}(\underline{r}_i)M_{nmk}^B(\underline{r}-\underline{r}_i) +$$

$$i_{nmk3}(\underline{r}_i)N_{nmk}^B(\underline{r}-\underline{r}_i)] + \int_{Vi}\int_{D} n(\underline{r}_j, \underline{a}_j)g(\underline{r}_j, \underline{a}_j, \underline{r}_i, \underline{a}_i)$$

$$\sum_{nmk}\left[\left\{\sum_{rst} T_{rst1}^{nmk1}(\varrho, m, \underline{a}_j)\langle e_{rst1}(\underline{r}_j; \underline{a}_j)\rangle\right\}\right.$$

$$\sum_{v\mu} A_{v\mu}^{nmk1} L_{v\mu k}^B(\underline{r}-\underline{r}_i) +$$

$$\left\{\sum_{rst} T_{rst2}^{nmk2}(\varrho, m, \underline{a}_j)\langle e_{rst2}(\underline{r}_j; \underline{a}_j)\rangle\right\}$$

$$\sum_{v\mu}[A_{v\mu}^{nmk2}M_{v\mu k}^B(\underline{r}-\underline{r}_i) + A_{v\mu}^{nmk3}N_{v\mu k}^B(\underline{r}-\underline{r}_i)] +$$

$$\left\{\sum_{rst} T_{rst3}^{nmk3}(\varrho, m, \underline{p}_j)\langle e_{rst3}(\underline{r}_j; \underline{a}_j)\rangle\right\}$$

$$\sum_{v\mu}[A_{v\mu}^{nmk3}M_{v\mu k}^B(\underline{r}-\underline{r}_i) +$$

$$\left. A_{v\mu}^{nmk2}N_{v\mu k}^B(\underline{r}-\underline{r}_i)]\right] d\underline{a}_j dv_j$$

It is now straightforward, applying the mutual orthogonality of the functional sets $\{\underline{L}_{nmk}\}$, $\{\underline{M}_{nmk}\}$, $\{\underline{N}_{mk}\}$, to arrive to the following equation:

$$\langle e_{nmkq}(\underline{r}_i; \underline{a}_i) \rangle = \qquad (27)$$

$$i_{nmkq}(\underline{r}_i) + \sum_{rstu} \int_{V_i} n(\underline{r}_j) \left\{ \int_D f_n(\underline{a}_j) g(\underline{r}_j, \underline{a}_j, \underline{r}_i, \underline{a}_i) T^{nmkq}_{rstu}(\underline{\varrho}, \underline{m}, \underline{a}_j) \right.$$

$$\left. \langle e_{rstu}(\underline{r}_j; \underline{a}_j) \rangle d\underline{a}_j \right\} \sum_{\nu\mu} A^{nmkq}_{\nu\mu}(\underline{r}_j - \underline{r}_i) dv_j$$

Prior equations 13 through 27 complete the disclosure of block 27 in FIG. 2. Taking now the configurational average with respect to the attributes of particle i (to implement block 28, FIG. 2) it is found:

$$\langle\langle e_{nmkq}(\underline{r}_i)\rangle\rangle = i_{nmkq}(\underline{r}_i) + \sum_{rstu} \int_{V_i} n(\underline{r}_j) \langle T^{nmkq}_{rdtu}(\underline{\varrho}, \underline{m}, \underline{r}_j) \rangle \qquad (28)$$

$$\langle\langle e_{rstu}(\underline{r}_j)\rangle\rangle \sum_{\nu\mu} A^{nmkq}_{\nu\mu}(\underline{r}_j - \underline{r}_i) dv_j \langle T^{nmkq}_{rstu}(\underline{\varrho}, \underline{m}, \underline{r}_j)\rangle =$$

$$\int_{D2} f_n(\underline{a}_j) \langle g(\underline{r}_j, \underline{a}_j, \underline{r}_i) \rangle T^{nmkq}_{rstu}(\underline{\varrho}, \underline{m}, \underline{a}_j) d\underline{a}_j \langle g(\underline{r}_j, \underline{a}_j, \underline{r}_i) \rangle =$$

$$\int_{D1} f_n(\underline{a}_i) g(\underline{r}_j, \underline{a}_j, \underline{r}_i, \underline{a}_i) d\underline{a}_i$$

The equalities $\langle e_{rstu}(\underline{r}_j; \underline{a}_j)\rangle = \langle e_{rstu}(\underline{r}_j; \underline{a}_i)\rangle = \langle\langle e_{rstu}(\underline{r}_j)\rangle\rangle$ that result from the non-segregation hypothesis and the "quasi-crystalline" approximation have been applied. Domains D1 and D2 are governed by the non-interpenetrability of the particles because some properties (like size and shape) relate to the space occupancy of the particles. It is worth noting the radical difference between equation 28 (for the case when only the attribute size is considered) and the prior art, e.g., [36] Varadan et al in page 379 of "A Multiple Scattering Theory for Elastic Wave Propagation in Discrete Random Media", J. Acoust. Soc. Am., 77(2), February 1985, where the authors suggest that a distribution of sizes could be dealt with by replacing the transition operator T by $$\langle T \rangle = \int_0^\infty T(d) f_n(d) dd.$$

Even recalculating the correlation integral for each size of the distribution as the authors suggest as more accurate, it is clear that such an approach can only constitute a coarse approximation to the complex intricate relation between <T>, T, $f_n$, <g>, and g shown in equation 28. They agree only when $\langle g(\underline{r}_j, \underline{a}_j, \underline{r}_i, \underline{a}_i)\rangle \equiv 1$ —a condition not true even under the "hole correction", i.e. when CF(r)≡1. The main reason for this disparity resides in the prior-art never recognizing that when the population has a distribution of attributes, so it does the arbitrary particle chosen as fixed in space so as to develop the stochastic field equations. Consequently, the second configurational average with respect to the attributes is paramount to arrive to the correct final dispersion equations.

Before proceeding towards the final dispersion equations for the particulate, let us see how equation 28 transforms for simpler cases already contemplated in the prior art. For the simpler but important basic case in which all scatterers are identical with attribute vector $\underline{a}_0$, i.e. —using the Dirac's δ function—$f_n(\underline{a}_k)=\delta(\underline{a}_k-\underline{a}_0)$, the following equalities are valid:

$$\langle g(\underline{r}_j, \underline{a}_j, \underline{r}_i) \rangle = \int_{D1} \delta(\underline{a}_i - \underline{a}_0) g(\underline{r}_j, \underline{a}_j, \underline{r}_i, \underline{a}_i) d\underline{a}_i \qquad (29)$$

$$= g(\underline{r}_j, \underline{a}_j, \underline{r}_i, a_0)$$

$$\langle T^{nmkq}_{rstq}(\underline{\varrho}, \underline{m}, \underline{r}_j)\rangle = \int_{D2} \delta(\underline{a}_j - \underline{a}_0) g(\underline{r}_j, \underline{a}_j, \underline{r}_i, a_0) T^{nmkq}_{rstq}(\underline{\varrho}, \underline{m}, \underline{a}_j) d\underline{a}_j$$

$$= g(\underline{r}_j, \underline{a}_0, \underline{r}_i, a_0) T^{nmkq}_{rstq}(\underline{\varrho}, \underline{m}, a_0)$$

Further assuming the particle concentration is spatially uniform, i.e. $n(\underline{r}_j)=n_0$, and the pair-correlation being a function of only the distance between the identical particles and their identical size D, equation 28 becomes:

$$\langle\langle e_{nmkq}(\underline{r}_i)\rangle\rangle = i_{nmkq}(\underline{r}_i) + n_0 \sum_{rstq} T^{nmkq}_{rstq}(\underline{\varrho}, \underline{m}, a_0) \qquad (30)$$

$$\int_{V_1} g(|\underline{r}_j - \underline{r}_i|, D) \langle\langle e_{rstq}(\underline{r}_j)\rangle\rangle \sum_{\nu\mu} A^{nmkq}_{\nu\mu}(\underline{r}_j - \underline{r}_i) dv_j$$

The above equation is found in the prior-art literature for identical scatterers with the following caveats: a) the configurational averaging with respect to $\underline{a}_i$ (second angular bracket) does not appear though, being $\underline{a}_i = \underline{a}_j \forall i, j$ when scatterers are identical, it is immaterial; b) the concept behind the existence of subscript k (to, e.g., contemplate thermal and viscous-inertial waves) is definitely inexistent in the prior art. This latter feature is essential for an accurate modeling of multiple scattering in the acoustical and elastodynamic cases. It is clear then that the description of the multiple scattering phenomena in particulate composites provided by this invention is considerably more general and accurate than those in the existing prior art. Besides, as it should be, upon the consideration of simpler specific cases, our equations reduce to those well known by the skilled in the art. The assertion regarding accuracy will be further proved with experimental data.

Equation 28 constitutes a linear system of equations with $\langle\langle e_{nmkq}(\underline{r}_i)\rangle\rangle$ as the unknowns (the so-called dispersion equations). In order to solve it, some practical assumptions are needed. First assumption is that the coherent exciting field $\langle\langle e_{nmkq}(\underline{r}_i)\rangle\rangle$ is that of a plane wave with an effective propagation constant $K_k$. In symbols: a solution of the form $\langle\langle e_{nmkq}(\underline{r}_i)\rangle\rangle = X_{nmkq} \exp(iK_k z_i)$ is searched for. Replacing in equation 28 it is obtained:

$$X_{nmkq} \exp(iK_k z_i) = i_{nmkq}(\underline{r}_i) + n_0 \sum_{rstu} X_{rstu} \exp(iK_k z_i) \qquad (31)$$

$$\int_{V_i} \langle T^{nmkq}_{rstu}(\underline{\varrho}, \underline{m}, \underline{r}_j)\rangle \exp(iK_t(z_j - z_i)) \sum_{\nu\mu} A^{nmkq}_{\nu\mu}(\underline{r}_j - \underline{r}_i) dv_j$$

Using equation 25 for the Coefficients $A^{nmkq}_{\nu\mu}(\underline{r}_j - \underline{r}_i)$ and noting the axial symmetry of the problem that renders only terms independent of the azimuthal angle (m=μ) as contributors to the integral, it is obtained:

$$X_{nmkq}\exp(iK_t z_t) = i_{nmkq}(\underline{r}_i) + \qquad (32)$$
$$n_0 \sum_{rstu} X_{rstu} \exp(iK_t z_t) \sum_{\nu\mu} \sum_p a_q(n, m, \nu, \mu, p) I_{s\mu p}(K_t, k_t)$$

$$I_{s\mu p}(K_t, k_t) = \delta_{s\mu} \int_{V_i} \langle T_{rstu}^{nmkq}(\underline{\varrho}, \underline{m}, \underline{r}_j) \rangle \exp(iK_t(z_j - z_i))$$
$$h_p(k_t|\underline{r}_j - \underline{r}_i|) P_p(\cos\theta_{ij}) \exp(i(s-\mu)\phi_{ij}) d\nu_j$$

Where $\delta_{ij}$ is the Kronecker symbol which value is 1 for i=j and 0 for i≠j. Because both the unknown coherent wave in the composite and the set of basis functions verify the Helmholtz equation, the integral can be rewritten as:

$$I_{s\mu p}(K_t, k_t) = \delta_{s\mu} \int_{r \geq b} \langle T_{rstu}^{nmkq}(\underline{\varrho}, \underline{m}, \underline{r}_j) \rangle \exp(iK_t z) h_p(k_t r) P_p(\cos\theta_{ij}) d\nu$$
$$= \{1/(K_t^2 - k_t^2)\} \int_{r \geq b} \langle T_{rstu}^{nmkq}(\underline{\varrho}, \underline{m}, \underline{r}_j) \rangle [\exp(iK_t z)\nabla^2\{h_p(k_t r) P_p(\cos\theta_{ij})\} - \nabla^2\{\exp(iK_t z)\} h_p(k_t r) P_p(\cos\theta_{ij})] d\nu$$

And using Gauss's theorem of divergence so as to convert the volume integral into a surface integral, the value for the integral can be expressed as the sum of three terms $I_p^c$, $I_p^d$ and $I_e^p$ as follows:

$$I_p^c(K_t, k_t) = \left\{\frac{2\pi i}{k_t^2(K_t - k_t)}\right\} i^p \exp(iK_t z_i) \exp(-iK_t z_i) \qquad (33)$$

$$I_p^d(K_t, k_t, b) = -\left\{\frac{4\pi b^2}{(K_t^2 - k_t^2)}\right\} i^p \left[\frac{\partial}{\partial b} h_p(k_t b) j_p(K_t b) - h_p(k_t b) \frac{\partial}{\partial b} j_p(K_t b)\right]$$

$$I_p^e(K_t, k_t, b) = \int_b^\infty r^2 [\langle T_{rstq}(\underline{\varrho}, \underline{m}, r) \rangle - 1] h_p(k_t r) j_p(K_t r) dr$$

It is worth noting once more the difference in this case between our $I_p^e(K_t, k_t, b)$ and the corresponding term in the prior-art, e.g. term $M_p(k, K|b)$ in page 554 of [28] L. Tsang et al, "Multiple Scattering of Acoustic Waves by Random Distribution of Discrete Spherical Scatterers with the Quasicrystalline and Percus-Yevick Approximation", J. Acoust. Soc. Am. 71(3), March 1982. In this prior-art publication our term $<T_{rstq}(\underline{\varrho}, \underline{m}, r)>$ does not exit; it is simply replaced by the transition matrix times the pair correlation function, a replacement that is only valid for identical scatterers.

Finally, without loss of generality, the coordinate system can be selected such that the z-axis is in the direction of propagation of the incident wave and the y-axis is in the direction of the displacement vector for the transversal component of the incident wave. Consequently, a generic representation for a plane incident wave (acoustic, electromagnetic or elastic) of unity intensity with respect to the point $\underline{r}_i$ is:

$$\underline{I}(\underline{r}-\underline{r}_i) \exp(ik_2 z_i) \exp(ik_2(z-z_i))\underline{e}_y + \exp(ik_1 z_i) \exp(ik_1(z-z_i))\underline{e}_z\underline{r} = x\underline{e}_x + y\underline{e}_y + z\underline{e}_z \qquad (34)$$

Let us now explicitly express $i_{nmkq}(\underline{r}_i)$ in spherical coordinates [1].

$$i_{nm1q}(\underline{r}_i) = \{\exp(ik_1 z_i)/ik_1\}(2n+1)i^n \delta_{m0}\delta_{q1}$$

$$i_{nm21}(\underline{r}_i) = 0 \quad i_{nm22}(\underline{r}_i) = \{\exp(ik_2 z_i)/2\} \{(2n+1)i^n / (n(n+1))\} \{\delta_{m1} - n(n+1)\delta_{m,-1}\}$$

$$i_{nm23}(\underline{r}_i) = \{\exp(ik_2 z_i)/2\} \{(2n+1)i^n/(n(n+1))\} \{\delta_{m1} + n(n+1)\delta_{m,-1}\} \qquad (35)$$

When placed into equation 32 the first term in equation 33 leads to the cancellation of the incident wave as per the well-known Ewald-Oseen extinction theorem expressed in the following equation:

$$0 = i_{nmkq}(\underline{r}_i) + n_0 \sum_{rstu} X_{rstu} \sum_{\nu\mu} \sum_p a_q(n, m, \nu, \mu, p) \left\{\frac{2\pi i}{k_t^2(K_t - k_t)}\right\} i^p \qquad (36)$$

From the above equation the multiple-scattering propagation constants for the particulate composite are obtained as a function of the propagation constants of the host medium, the particle concentration, and the amplitudes $X_{rstu}$. Placing now the second and third terms of equation 33 into equation 32, the following generic expression for the Lorentz-Lorenz law is obtained:

$$X_{nmkq} = i_{nmkq}(\underline{r}_i) + \qquad (37)$$
$$n_0 \sum_{rstu} X_{rstu} \sum_{\nu\mu} \sum_p a_q(n, m, \nu, \mu, p)\{I_p^d(K_t, k_t) + I_p^e(K_t, k_t)\}$$

The last equation constitutes an infinite system of simultaneous homogeneous equations in complex numbers for the unknown amplitudes $X_{nmkq}$ that can be truncated to a finite system upon employment of a suitable convergence criterion. A non-trivial solution will exist only when the determinant of the system is zero. The propagation constants for the particulate system are then determined by finding the value of $K_t$ for which the determinant is null. Any suitable algorithm for accurately finding the complex root of a complex function could be used in this invention (e.g. from "Collected Algorithms from ACM", The Association for Computing Machinery, or W. H. Press et al, "Numerical Recipes, The Art of Scientific Computing", Cambridge Press, 1988). Knowing the propagation constants for the composite, all its attributes (attenuation, scattering, velocity, physical properties, etc) can be straightforwardly determined. For instance, the expected value $<\chi>$ for the adiabatic compressibility of the composite can be calculated from the formula $$\langle \chi \rangle = \frac{K^2 \chi_m \rho_m}{k_m^2 \langle \rho \rangle}$$

where subscript m stands for host medium, $<\rho>$ is the average density of the composite, and K and k are the composite and host medium propagation constants respectively. Equations 31 through 37, plus the above prior-art references for their standard computer programming, complete the disclosure of block 30 in FIG. 2 and therefore finish the full disclosure of the METAMODEL™ Prediction and Inversion Engines 21 and 22.

Experimental Validation of the METAMODEL™ Prediction Engine 21

Well-controlled experimental data in concentrated particulates are not abundant in the technical literature. Some data for electromagnetic and elastic waves, and their successful comparison with predictions from specific versions of the analytical theory can be found in [31,32,33,36,37,42]. Because the present prediction engine is the result of a generic employment of the analytical theory plus the novel features already described, those prior successes can be readily considered as a partial validation for the prediction engine of this invention. However, this by itself would not be—obviously—enough. The most appropriate field to fully validate the current invention with its novel features is in Acoustics because of: a) the diversity of physical phenomena occurring when a sound wave interacts with particulates, b) accurate acoustic data have been made available only during the last decade due to the recent commercial advent of acoustic spectrometers, and c) it is the successful integration of viscous-inertial, thermal diffusion, surface tension, and viscoelasticity phenomena into the fundamental statistical treatment of multiple-scattering what constitutes the gist for the prediction and inversion of the current invention. Consequently, it is herein disclosed a considerable amount of acoustic experimental data that solidly validate the accuracy and operability of the METAMODEL™ Prediction Engine 21.

Acoustical data in suspensions and emulsions were gathered using the acoustic spectrometer function of a particle size analyzer (ULTRASIZER™) manufactured by Malvern Instruments Ltd of the United Kingdom. In this instrument, the attenuation coefficient of ultrasound waves in a frequency range from 1 MHz to 150 MHz is measured with accuracy better than 5%. Concentration ladders from low concentrations ($C_v \leq 1\%$), where both the standard single-scattering model and the prediction engine of the current invention perfectly agree, up to concentrations as high as 30% by volume were carefully made avoiding aggregation. For every measured sample, only measurements for concentrations above 10% are shown in this disclosure because—in the acoustics field—only at such high concentrations is when the drastic improvement on accuracy achieved by the current invention is easily visible.

Figure 3:
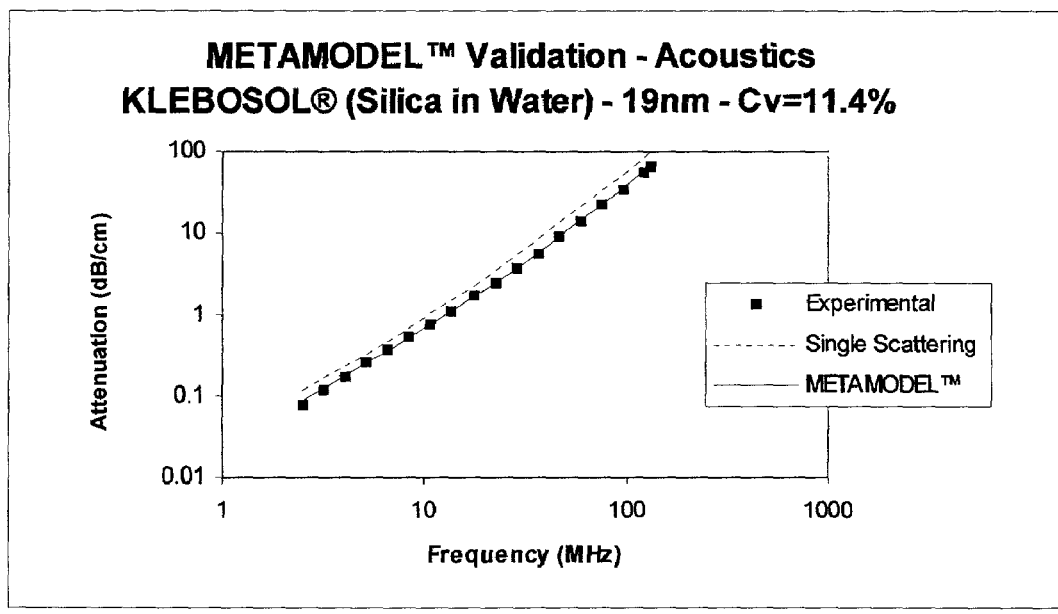
FIG. 3 validates the prediction engine for an extremely fine dispersion of silica particles (19 nm) used in the semiconductor industry for polishing, at a particle concentration of $C_v=11.4\%$ FIG. 4 validates the prediction engine for an extremely fine dispersion of silica particles (19 nm) used in the semiconductor industry for polishing at $C_v=17.1\%$ FIG. 5 validates the prediction engine for a dispersion of standard silica particles (100 nm±30 nm) at $C_v=10.0\%$ FIG. 6 validates the prediction engine for a dispersion of standard silica particles (100 nm ±30 nm ) at $C_v=30.0\%$ FIG. 7 validates the prediction engine for a dispersion of standard silica particles (300 nm±30 nm ) at $CV=16.0\%$ FIG. 8 validates the prediction engine for a dispersion of standard silica particles (300 nm±30 nm) at $C_v=24.0\%$ FIG. 9 validates the prediction engine for a dispersion of standard silica particles (450 nm±30 nm ) at $C_v=10.0\%$ FIG. 10 validates the prediction engine for a dispersion of standard silica particles (450 nm±30 nm ) at $C_v=30.0\%$ FIG. 11 validates the prediction engine for a broad distribution of soy oil droplets in water (0.06 µm to 2 µm) at $C_v=10.6\%$
Figure 4:
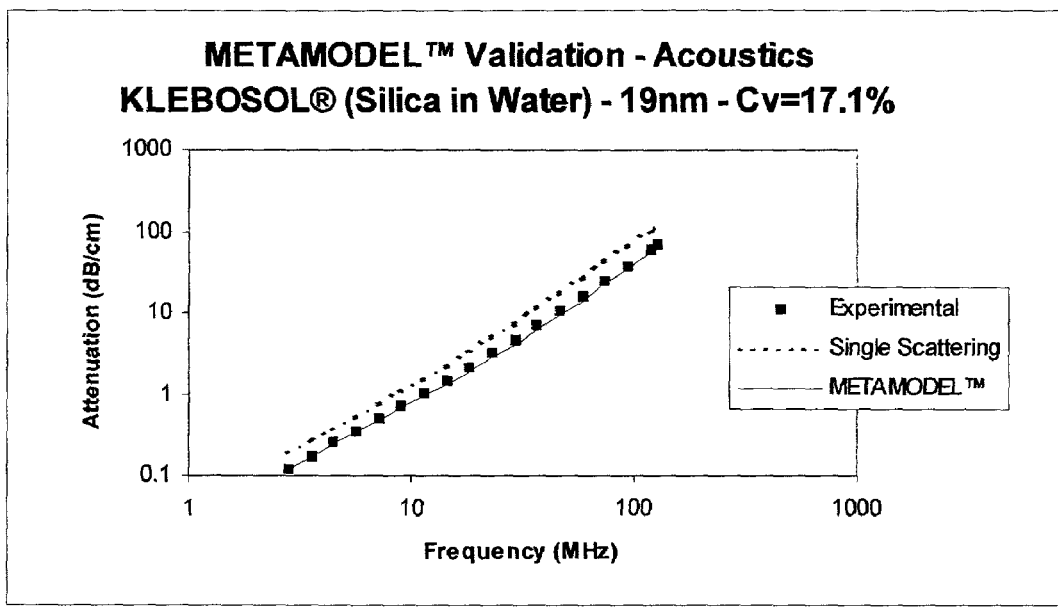

FIG. 3 and FIG. 4 correspond to an extremely fine dispersion of silica particles (KLEBOSOL® 30R12) used in the semiconductor industry for silicon wafer polishing. The manufacturer gives only an approximate value for the mean size of around 12 nm. Using the ULTRASIZER™ at the optimal concentration for maximum accuracy, its actual mean size was determined as 19 nm. With this value for the size, the attenuation spectrum at high concentrations was calculated with the METAMODEL™ Prediction Engine 21 and compared with the experimental spectra. Predictions based on the standard single-scattering model are also shown on the graphs in order to assess the significance of multiple-scattering effects. FIG. 3 and FIG. 4 correspond to $C_v=11.4\%$ and $C_v=17.1\%$ respectively. Agreement between experimental data and METAMODEL™ predictions is within 10% throughout the frequency range, with a typical accuracy of about 5%. Nissan Chemical America Corp. manufactures silica dispersions with very narrow size distribution and well-controlled mean size.

Figure 5:
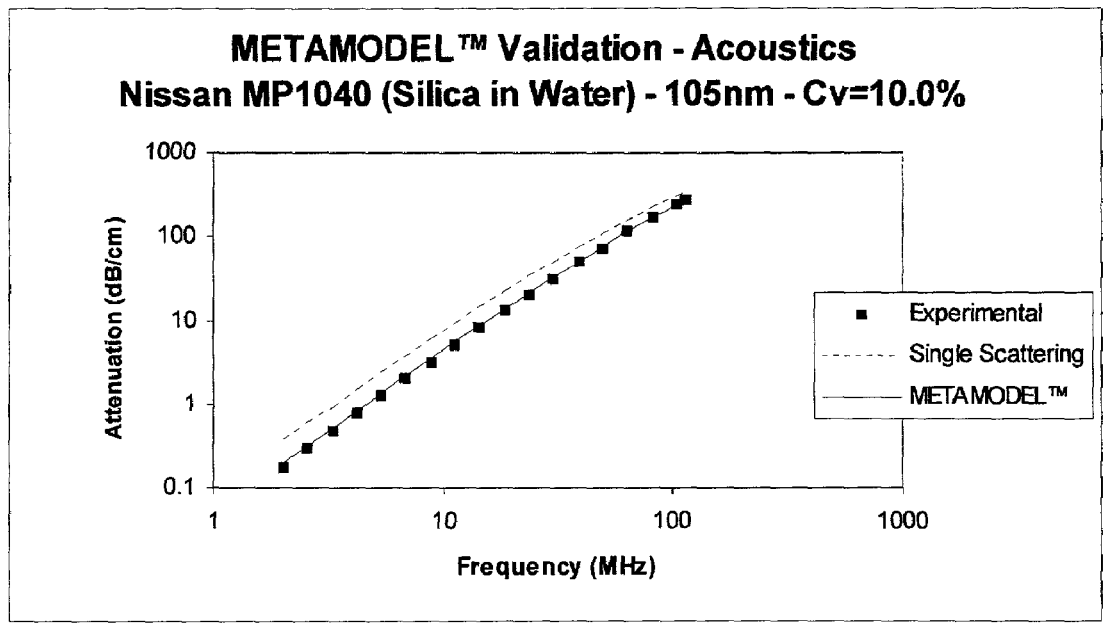
Figure 6:
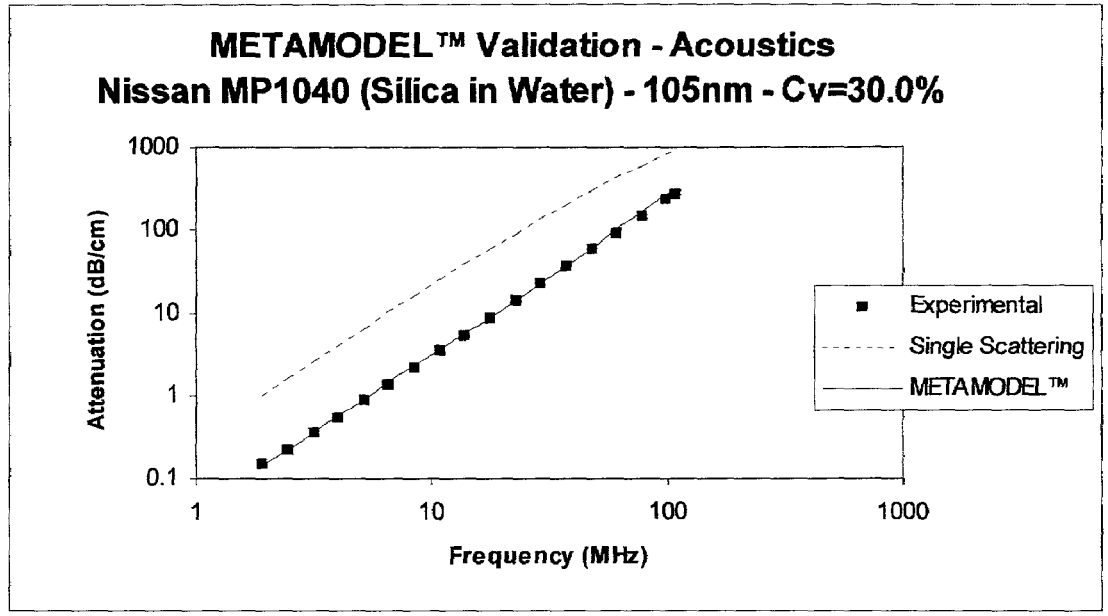
Figure 7:
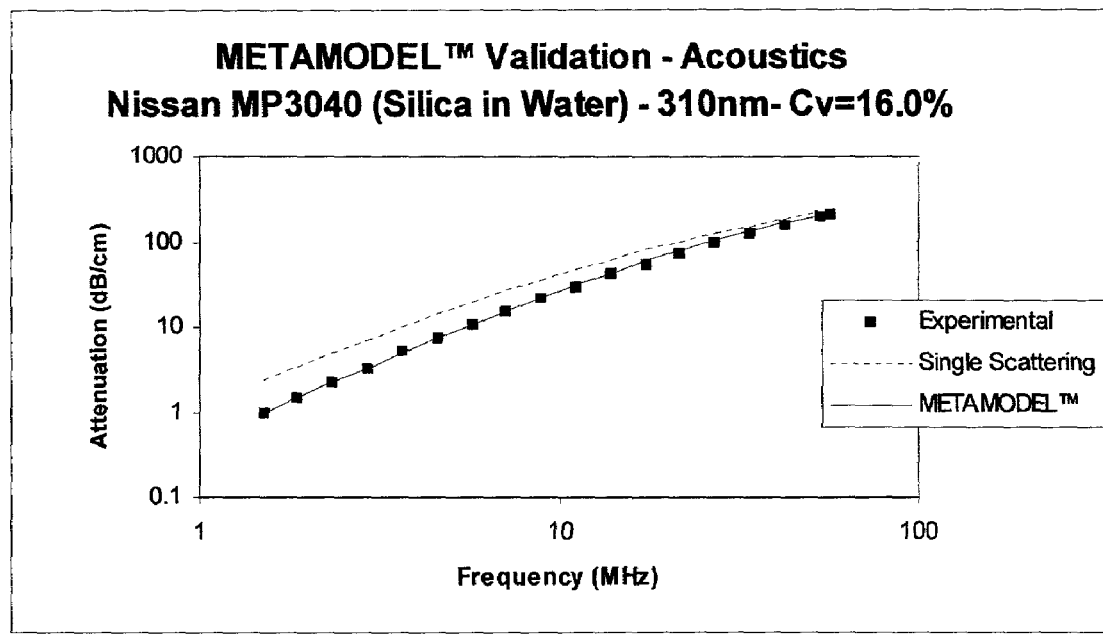
Figure 8:
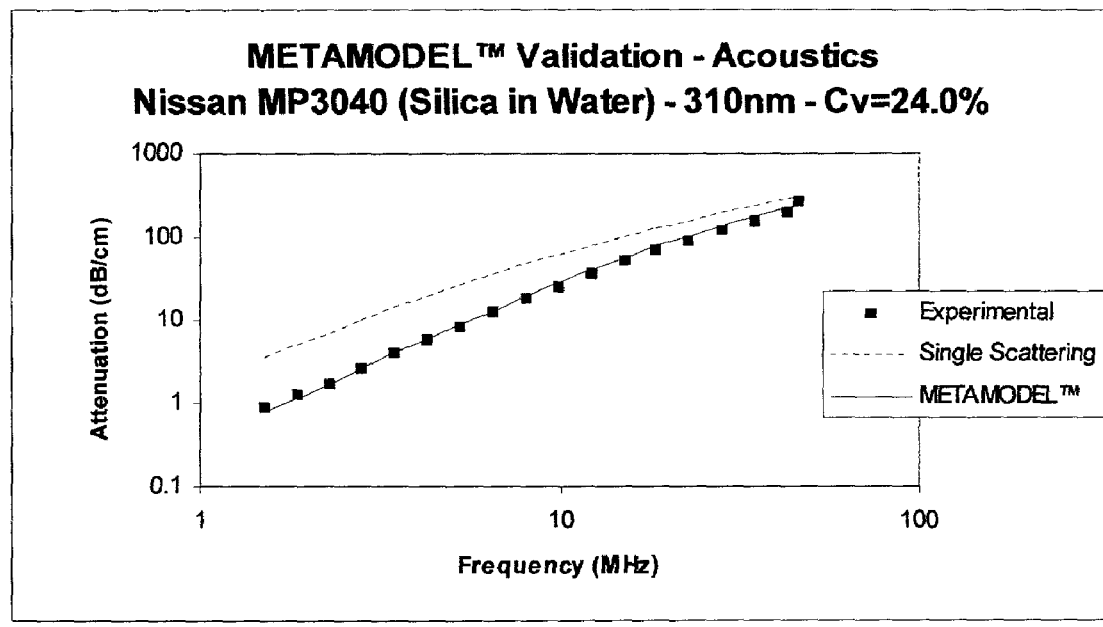
Figure 9:
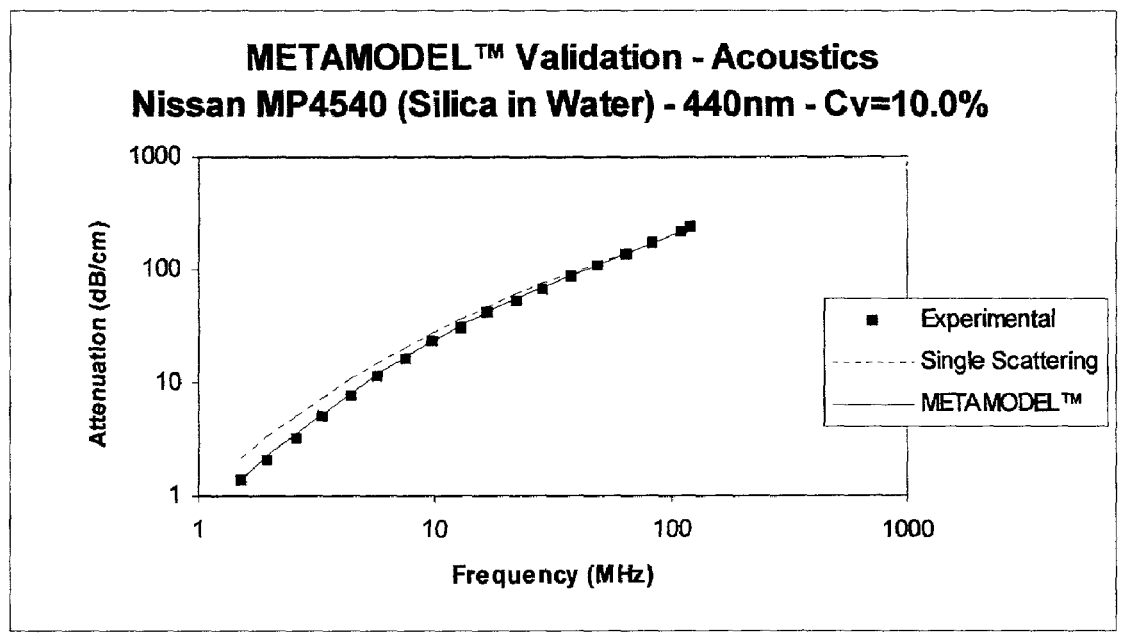
Figure 10:
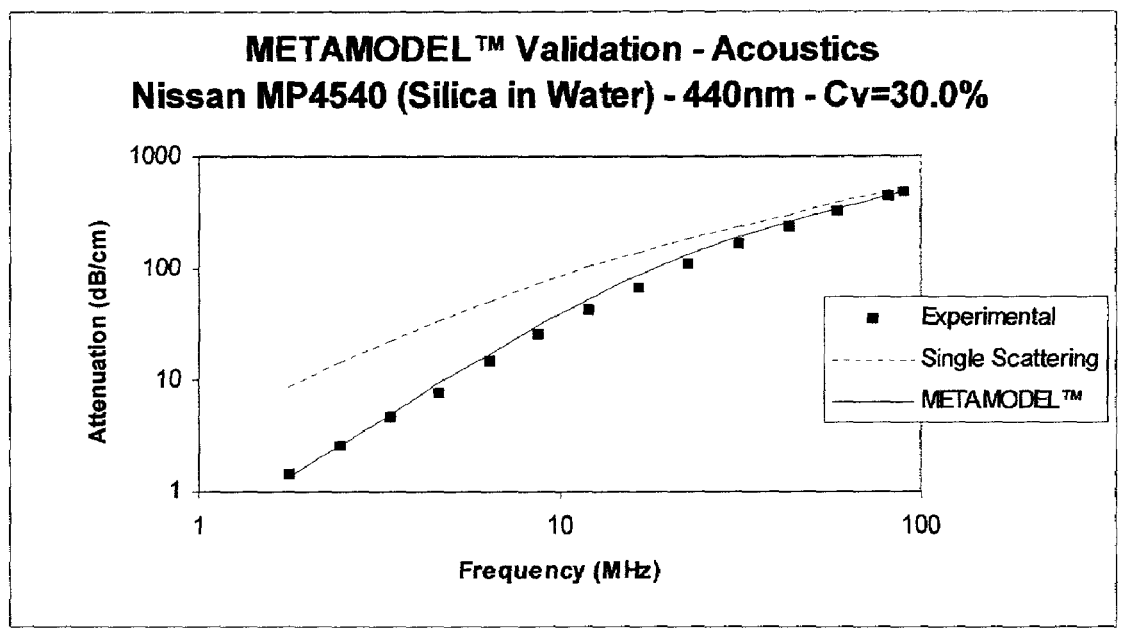
Figure 11:
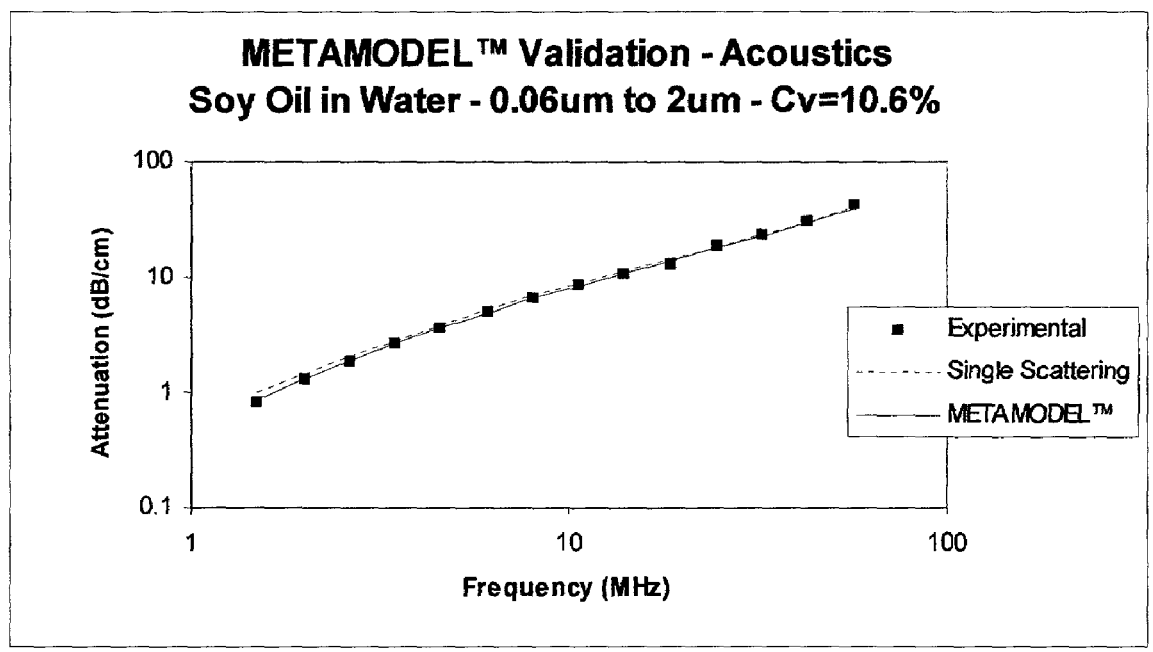

FIG. 5 and FIG. 6 correspond to a product with a size specified as 100 nm±10 nm. The actual size was determined with the ULTRASIZER™ at a concentration for maximum accuracy obtaining 105 nm. With this value for the size, the prediction engine for this invention was run at high concentrations and compared with the actual measured spectra. FIG. 5 and FIG. 6 are for concentrations of 10% and 30% respectively. Agreement is again excellent (well below 10%). FIG. 7 and FIG. 8 are for a product specified by the manufacturer as 300 nm±30 nm. The ULTRASIZER™, operated at the optimum concentration, delivered 310 nm. Using this value for the size, FIG. 7 and FIG. 8 show a very good agreement between METAMODEL™ and the actual spectra taken at 16% and 24%. The last Nissan product is stated to have a mean size of 450 nm±45 nm. FIG. 9 and FIG. 10 are, by now, self-explanatory, confirming once more the predicting power of the current invention. Finally, FIG. 11 corresponds to a broad distribution of soy oil droplets in water at about 11% concentration. As expected for emulsions, multiple scattering effects at this relatively high concentration are still not very significant [48]. Notwithstanding, there is a visible small systematic deviation of the actual measured spectrum from the single-scattering prediction at the low frequency end. The METAMODEL™ Prediction Engine once more demonstrates its prediction power by following almost perfectly (better than 5%) the experimental data at low frequency.

Detailed Description/Operation of the SCATTERER™ Graphical Interface 23

Due to the remarkable advance of computer technology during the last two decades, de facto industry standards for graphical user interfaces have developed and are well known and employed in the implementation of any computer-based system. Hierarchies of windows, icons, option and command buttons, checkbox controls, context menus, image controls, tab-strip controls, tables, graphs, tool-tips, on-line help, etc are common place in the attempt to improve the ergonomics of human interaction with machines. Upon installation of the attached CD-R disks in a suitable computer, the "look and feel" of a preferred embodiment for this invention can be experienced. Virtually an infinite number of interfaces with different "looks and feels" could be designed, and still all of them achieving the essential object of this important component for the current invention. With that proviso, and for the sake of a better disclosure of the features and operation of this invention, the structure, materials, and operation of the Graphical Interface component 23 will be described by direct reference to the preferred embodiment.

Interaction with the human operator starts by allowing her to select amid three suites: Acoustics, Electromagnetics, and Elastodynamics. After the desired selection, the appearance of these suites to the user is basically the same, except for some different variables and default conditions corresponding to well-established practices in each field. For instance, in acoustics it is customary to refer to the frequency of the wave, while in electromagnetics it is the wavelength the used equivalent operating attribute; in acoustics the frequency is most commonly varied and the scattering angle is fixed, while in light scattering exactly the opposite is normally practiced, and so forth. The concept of a tool-tip-text (brief explanation of the purpose of each control) is used throughout the interface to help the operator to quickly navigate the system and familiarize with all its features. On-line help is also available. A main screen for the suite appears and displays, on its left side, several menus for a) selecting different mathematical models, b) availability of experimental data, c) settings for graphical and tabular display of results, and d) buttons for starting a simulation experiment, stopping it, exiting the suite going back to the original suite selection screen, and a progress bar to monitor the experiment evolution once started. On the right topside of the same screen there is a table where the results of the experiment are displayed and, on the right bottom side, a graph depicts the same results. The table can be set to be refreshed in real-time while the simulation experiment is undergoing, or to be only updated at the end. The table can also be expanded, contracted, printed, and hidden. The graph can be refreshed either in real-time or at the end of the experiment, expanded, contracted, printed, depicted in two or three dimensions, and the scales in the three axes can be selected as linear or logarithmic. The 3D graph can be rotated at will in real-time to examine any particular structure by simply dragging the mouse. By double-clicking on the graph, all graph features can be changed to suit operator's needs and appeal. Different mathematical models can be selected from a menu list of single and multiple-scattering models employed for the last three or four decades (ECAH, Mie, Waterman & Truell, Twersky, etc.) with the purpose of comparing their accuracy with the last option in the menu which is the model for the current invention (METAMODEL™). The first model (Lamb-Epstein-Urick-Flammer) is a well-known combination of explicit approximations to the solution of the single-scattering wave equations. The rest of the models are fundamental. Several models can be selected as part of a single experiment by checking all the desired ones. Right-clicking on all single-scattering models but the first one opens a dialog window that allows the operator to either select full-convergence or choose the maximum number of terms to be used in the series expansion of the fields (the range for the index n in the specification for the prediction engine). A recommended minimum for accuracy is also shown on the dialog screen. This feature permits the researcher to understand the convergence intricacies for different regimes, particle size, frequency, etc. Right clicking on all multiple-scattering models but the METAMODEL™ one opens a dialog window that, besides the convergence feature, allows the operator to select the medium/particle signature, e.g. the Mie Model if in the electromagnetics suite. Right clicking on the METAMODEL™ model, a dialog screen appears that, when the control button is set to manual, entitles the researcher to set, besides the medium/particle signature and the convergence criterion, the following parameters for the pair-correlation function: a) amplitude, b) oscillation frequency, and c) vanishing rate. For each one of these variables the user can set a minimum, a maximum, and a number of values in the range. Upon starting the experiment, predictions for each one of those values will be conducted and results stored for post-processing and viewing.

Hiding the table unveils three menu frames. The one at the top has two command buttons, one for specifying the nature of the phases of the composite, and the other for specifying the particle size distribution and concentration of the particulate phase. The two frames at the bottom permit the user to set the minimum, maximum, number of values, and scale for the wave frequency (wavelength if in the electromagnetic suite) as well as for the scattering angle. The legend on the command button at the left side of the top frame corresponds to the nature of the phases (e.g. "Titania in Water") and, when clicking on it a dialog window appears on the screen. Up to two different types of particles in one type of host medium can be specified from a database of materials. Physical properties for the selected materials are displayed in a folder-like tab-strip control. New types of materials can be easily created with their physical properties -in a selected system of physical units- typed by the researcher and stored into a database of materials. Minimum, maximum, scale and number of values in the range to be use in the simulation experiment can also be selected. Clicking on the Size Distribution/Concentration command button pops up a dialog screen for setting the size distribution and concentration of the particulate phase. Minimum, maximum, scale and number of values for the particle concentration can be set by the operator. Regarding the particle size distribution, two populations can be specified (each made up of the same or different particle material) and mathematically combined. Each population distribution can be modeled using a lognormal distribution. Minimum, maximum, scale, and number of values for the geometric mean and deviation parameters for each population can be selected. As an ergonomic feature to familiarize the user with this modeling of size distributions, three real images depicting special cases of a monosize distribution, a wide unimodal distribution, and a bimodal distribution are shown at the top this screen and, when clicking on them the distribution parameters are automatically set and displayed. Other distribution models besides the lognormal for each population can obviously be added to the interface if necessary to represent actual particle size distributions for special cases. Clicking on the available option button in the Experimental Data frame triggers the appearance of a dialog screen where: a) existing experimental data can be retrieved in different formats (binary, ASCII text files, databases, etc); b) Existing experimental data can be typed into the computer and stored into its data base as a text file. Having completely defined a simulation experiment by specifying all the attributes of the constituent phases, their ranges and discrete values, and the operating variables, the operator can start the experiment by clicking on the execute button at the bottom left corner of the main screen. The experiment can be very complex and demanding on computer resources depending upon the number of attributes that are to be varied and the number of points for each of them. Basic combinatorial calculations are done by the system and displayed with the progress bar so that the operator knows the status of the simulation experiment. Several thousand predictions can be easily performed in a typical experiment. Before, during, or at the end of an experiment, clicking on the Graph/Table Settings button triggers a menu to appear overlapping the Mathematical Models and Experimental Data menus. These settings decide what is it that the researcher wants to look at; it does not decide the nature (attributes to be changed and their ranges) of the simulation experiment. At its top the experimenter can select one of four attribute-axes (X, Y, Z, H). Clicking on one of them pops up a menu of physical attributes to be chosen for the particular axis. The Z-axis is used to display the attributes of the composite; the X, Y, and H axes are used to depict different attributes for the particulate and host phases as well as the operating conditions. In the preferred embodiment being described, there are fifty-four different physical attributes to be selected from for each of these three axes. If the graph is set as two-dimensional, the plot will depict Z as a function of X parameterized with Y; if three-dimensional the plot will show Z as a function of X and Y. The H-axis (Hyper-attribute) is a fourth-dimension attribute which effect on the simulation results can be graphically observed by varying its value using a sliding rule control after having clicked on the H-Attribute button, selected the desired attribute, and dragging on the sliding control. Table and graph will dynamically update as the operator slides the ruler through the range for the particular attribute selected. Clicking on the Z-axis button, displays a menu of physical attributes for the composite to be shown on that axis. Among them are: attenuation, velocity, intensity, scattering cross-section, physical properties of the composite, extinction efficiency, etc. All these alternative ways of viewing the relationship between different attributes can be pursued in real-time while a complex simulation experiment is undergoing.

SCOPE OF INVENTION

While my the above description contains much specificity, it should not be construed as limiting the scope of the invention, but rather as an exemplification of one preferred embodiment thereof. Many other variations are possible. Accordingly, the scope of the invention should be determined not by the embodiment illustrated, but by the appended claims and their legal equivalents.

I claim:

1. A computer-based method for enabling a human operator to conduct complex simulation, parametric studies, analysis and synthesis of systems in which there exists interaction between acoustic, electromagnetic or elastic waves and a composite of particulate phases included in a continuous phase, with physical attributes, the method comprising:
   predicting the physical attributes of said composite from knowledge of the physical attributes of constituent phases of the composite, using a mathematical model, to thereby obtain predictions that can be contrasted with actual experimental values;
   estimating a selected subset of said physical attributes of said constituent phases and composite from the knowledge of unselected subset of said physical attributes of said constituent phases and composite, to thereby obtain particle size distribution, concentration, and other said selected subset of physical attributes;
   connecting a computer to one or more commercially available spectrometers to measure the particle size distribution, concentration, and other said selected physical attributes of said constituent phases and composite;
   displaying the measured particle size distribution, concentration, and other said selected physical attributes on a graphical interface; and
   utilizing the measured particle size distribution, concentration, and other said selected physical attributes, to evaluate the composite of particulate phases included in a continuous phase.

2. The method as set forth in claim 1, wherein said mathematical model is based on analytical wave scattering theory.

3. The method as set forth in claim 1, wherein said mathematical model provides integrating viscous-inertial, thermal diffusion, surface tension, and viscoelasticity phenomena into a statistical treatment of multiple-scattering of said acoustic, electromagnetic, or elastic waves interacting with said composite.

4. The method as set forth in claim 1, wherein said predicting step further includes other mathematical models for assessing differences in accuracy for each one of said mathematical models when compared with actual experimental data.

5. The method as set forth in claim 1, wherein said composite has a particle concentration in excess of 10% by volume.

6. The method as set forth in claim 1, wherein said composite is comprised of solid inclusions in a solid host medium.

7. The method as set forth in claim 1, wherein said composite is comprised of solid particles suspended in a fluid host medium.

8. The method as set forth in claim 1, wherein said composite is comprised of fluid particles suspended in a fluid host medium.

9. The method as set forth in claim 1, wherein said composite is comprised of fluid particles suspended in a solid host medium.

10. A method of predicting physical attributes of a highly concentrated composite of particulate phases with known attributes included in a continuous phase with known attributes, in their interaction with acoustic waves, electromagnetic waves, or elastic waves, the method comprising:
    statistically describing through a probability density function an exciting field, a scattered field, and an incident field in said highly concentrated composite by averaging said exciting field, said scattered field, and said incident field throughout all possible spatial distributions of particles and all possible distributions of particle attributes;
    expressing deterministically the relation between the exciting field and the scattered field around a particle with mathematical formalism for all acoustic, electromagnetic, and elastic fields;
    statistically describing through a probability density function local spatial and attribute correlations between particles;
    expressing the exciting field around a fixed particle in terms of the incident field and the scattered field produced by the rest of the particles;
    averaging throughout all possible particle attribute distributions of the said fixed particle to thereby arrive to a set of integral equations relating said exciting field, said scattered field, and said incident field around all particles, wherein each integral equation comprises multiple integrals;
    calculating said integrals in the set of integral equations and specifying the operating conditions to thereby arrive to a finite set of homogeneous equations in said exciting field, said scattered field, and said incident field;
    finding a complex root for a determinant of said integral equations thereby to determine an expected propagation constant for said highly concentrated composite;
    calculating expected values of said physical attributes of said composite from said expected propagation constant and the known attributes of said particulate phases and said continuous phase; and
    displaying one or more of the expected values of said physical attributes of said composite; and
    utilizing one or more of the expected values of said physical attributes to evaluate the highly concentrated composite.

11. The method as set forth in claim 10, wherein the electromagnetic waves interact with suspensions of solid particles in a fluid host medium with particle concentrations in excess of 1% by volume.

12. The method as set forth in claim 10, wherein the electromagnetic waves interact with emulsions of fluid particles in a fluid host medium with particle concentrations in excess of 1% by volume.

13. The method as set forth in claim 10, wherein the acoustic waves interact with suspensions of solid particles in a fluid host medium with particle concentrations in excess of 10% by volume.

14. The method as set forth in claim 10, wherein the acoustic waves interact with emulsions of fluid particles in a fluid host medium with particle concentrations in excess of 10% by volume.

15. The method as set forth in claim 10, further including interfacing with existing acoustic and optical particle size measurement instruments.

16. An apparatus for enabling a human operator to conduct complex simulation, parametric studies, analysis and synthesis of systems in which there exists interaction between acoustic waves, electromagnetic waves, or elastic waves and a composite of particulate phases included in a continuous phase, with physical attributes, comprising:
   a general-purpose computer;
   data-carrier media to store, distribute, and install software and experimental data into said computer;
   predicting means, in combination with said computer and said carrier media, for predicting the physical attributes of said composite from a knowledge of the physical attributes of said particulate phases and said continuous phase, using a mathematical model, to thereby obtain predictions that can be contrasted with actual experimental values;
   inverting means, in combination with said computer and carrier media, for inverting said mathematical model whereby a selected subset of said physical attributes of said particulate phases, said continuous phase, and said composite can be estimated from the knowledge of the rest of said physical attributes of said particulate phases, said continuous phase, and said composite, to thereby obtain particle size distribution, concentration, and other said selected physical attributes;
   measuring means to measure the particle size distribution, concentration, and other said selected physical attributes of said constituent phases of the composite by analyzing experimental raw data produced by commercially available spectrometers;
   means for connecting said computer to the commercially available spectrometers; and
   means for displaying the measured particle size distribution, concentration, and other said selected physical attributes of said constituent phases of the composite on a graphical interface; and
   utilizing the measured particle size distribution, concentration, and other said selected physical attributes to evaluate the composite of particulate phases included in a continuous phase.

17. The apparatus as set forth in claim 16, wherein said predicting and inverting means are implemented as a dynamically linked library (DLL).

18. The apparatus as set forth in claim 16, wherein said predicting and inverting means are implemented through a Component Object Model (COM) server.

19. The apparatus as set forth in claim 16, wherein said data-carrier media comprises at least one compact disk or equivalent to store, distribute, and install said software and experimental data into said computer.

20. The apparatus as set forth in claim 16, wherein said data-carrier media comprises storing, distributing, and installing said software and experimental data into said computer through the Internet.

* * * * *